(12) United States Patent
Steer et al.

(10) Patent No.: US 6,544,972 B1
(45) Date of Patent: Apr. 8, 2003

(54) METHODS OF LIMITING APOPTOSIS OF CELLS

(75) Inventors: Clifford J. Steer, St. Paul, MN (US); Betsy T. Kren, Minneapolis, MN (US); Guangsheng Fan, Edina, MN (US); Cecilia M. P. Rodrigues, Lisbon (PT)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/509,309

(22) PCT Filed: Sep. 25, 1998

(86) PCT No.: PCT/US98/20168

§ 371 (c)(1),
(2), (4) Date: Aug. 15, 2000

(87) PCT Pub. No.: WO99/15179

PCT Pub. Date: Apr. 1, 1999

Related U.S. Application Data
(60) Provisional application No. 60/060,040, filed on Sep. 25, 1997.

(51) Int. Cl.⁷ ............................................. A61K 31/56
(52) U.S. Cl. ...................................... 514/182; 514/169
(58) Field of Search ........................................ 514/182

(56) References Cited

U.S. PATENT DOCUMENTS

| 5,656,725 A | 8/1997 | Chittenden et al. ......... 530/324 |
| 5,672,603 A | 9/1997 | Nakai et al. ................ 514/254 |

FOREIGN PATENT DOCUMENTS

| WO | WO 99/15179 | 4/1999 |

OTHER PUBLICATIONS

Koga et al., "Nuclear DNA Fragmentation and Expression of Bcl-2 in Primary Biiary Cirrhosis", Hepatology, 25, pp. 1077–1084, 1997.*
Adjei et al., "Cathepsin B Protease Activity But Not Interleukin 1 β–Converting Enzyme (ICE) Proteases Contributes to Camptothecin–Induced Apoptosis in a Human Hepatocellular Carcinoma Cell Line," Abstract 481, *Hepatology*, 24(4 Part 2):247A (1996).
Adjei et al., "Selective Induction of Apoptosis in Hep 3B Cells by Topoisomerase I Inhibitors: Evidence for a Protease–dependent Pathway That Does Not Activate Cysteine Protease P32," *J. Clin. Invest.*, 98(11):2588–2596 (1996).
Adjei et al., "Selective Induction of Apoptosis In A Human Hepatocellular Carcinoma (HCC) Cell Line By The Topoisomerase I Inhibitor Camptothecin," Abstract, *Gastroenterology*, 110(4 Suppl.):A483 (1996).
Beaufay et al., "Analytical Study of Microsomes and Isolated Subcellular Membranes from Rat Liver I. Biochemical Methods," *J. Cell Biol.*, 61:188–200 (1974).

Benedetti et al., "Subcellular changes and apoptosis induced by ethanol in rat liver," *J. Hepatology*, 6(2):137–143 (1988).
Bernardi, "Modulation of the Mitochondrial Cyclosporin A–sensitive Permeability Transition Pore by the Proton Electrochemical Gradient," *J. Biol. Chem.*, 267(13):8834–8839 (1992).
Boise et al., "bcl–x, a bcl–2–Related Gene That Functions as a Dominant Regulator of Apoptotic Cell Death," *Cell*, 74(4):597–608 (1993).
Botla et al., "Ursodeoxycholate Inhibits the Mitochondrial Membrane Permeability Transition (MMPT) Induced by Glycochenodeoxycholate: A Mechanism for Ursodeoxycholate Cytoprotection?" Abstract 316, *Hepatology*, 20(4 Part 2):175A (1994).
Botla et al., "Ursodeoxycholate (UDCA) Inhibits the Mitochondrial Membrane Permeability Transition Induced by Glycochenodeoxycholate: A Mechanism of UDCA Cytoprotection," *J. Pharmacol. Exp. Ther.*, 272(2):930–938 (1995).
Bouscarel et al., "Alteration of cAMP–mediated hormonal responsiveness by bile acids in cells of nonhepatic origin," *Am. J. Physiol.*, 268(6):G908–G916 (1995).
Bouscarel et al., "Ursodeoxycholic acid inhibits glucagon–induced cAMP formation in hamster hepatocytes: a role for PKC," *Am. J. Physiol.*, 268(2):G300–G310 (1995).
Calmus et al., "Differential Effects of Chenodeoxycholic and Ursodeoxycholic Acids on Interleukin 1, Interleukin 6 and Tumor Necrosis Factor–α Production by Monocytes," *Hepatology*, 16(3):719–723 (1992).
Carter et al., "Intracellular hydrogen peroxide and superoxide anion detection in endothelial cells," *J. Leukocyte Biol.*, 55(2):253–258 (1994).
Cathcart et al., "Detection of Picomole Levels of Hydroperoxides Using a Fluorescent Dichlorofluorescein Assay," *Anal. Biochem.*, 134:111–116 (1983).
Chazouillères et al., "Ursodeoxycholic acid for primary sclerosing cholangitis," *J. Hepatology*, 11(1):120–123 (1990).
Columbano, "Cell Death: Current Difficulties in Discriminating Apoptosis from Necrosis in the Context of Pathological Processes in Vivo," *J. Cell. Biochem.*, 58:181–190 (1995).
Committee on Care and Use of Laboratory Animals of the Institute of Laboratory Animal Resources Commission on Life Sciences, "NIH Publication No. 85–23: Guide for the Care and Use of Laboratory Animals," US Dept. of Health and Human Services, National Institute of Health, Bethesda, MD, 47 pages (1985).
Dupourque et al., "[20] Cytoplasmic and Mitochondrial Malate Dehydrogenases from Beef Kidney," *Methods Enzymol.* 13:116–122 (1969).

(List continued on next page.)

Primary Examiner—Dwayne C. Jones
(74) Attorney, Agent, or Firm—Mueting, Raasch & Gebhardt, P.A.

(57) ABSTRACT

Methods for limiting apoptosis in a cell population by contacting such cells with a hydrophilic bile acid, such as ursodeoxycholic acid (UDCA), salts thereof, and analogs thereof (e.g., glyco- and tauro-ursodeoxycholic acid).

29 Claims, 13 Drawing Sheets

OTHER PUBLICATIONS

Earnest et al., "Chemoprevention of Azoxymethane–induced Colonic Carcinogenesis by Supplemental Dietary Ursodeoxycholic Acid," *Cancer Res.*, 54(19):5071–5074 (1994).

Fan et al., "The retinoblastoma gene product inhibits TGF–β1 induced apoptosis in primary rat hepatocytes and human HuH–7 hepatoma cells," *Oncogene*, 12(9):1909–1919 (1996).

Fan et al., "Regulation of Apoptosis–Associated Genes in the Regenerating Liver," *Semin. Liver Dis.*, 18(2):123–140 (May 1998).

Goldin et al., "Apoptotic bodies in a murine model of alcoholic liver disease: reversibility of ethanol–induced changes," *J. Pathol.*, 171:73–76 (1993).

Haas–Kogan et al., "Inhibition of apoptosis by the retinoblastoma gene product," *EMBO J.*, 14(3):461–472 (1995).

Hanif et al., "Bile acids induce apoptosis in the colon of mice in vivo," Abstract A526, *Gastroenterology*, 110(4):156 (1996).

Harnois et al., "BCL–2 is Overexpressed and Alters the Threshold for Apoptosis in a Cholangiocarcinoma Cell Line," Abstract, *Gastroenterology*, 110(4):A1205 (1996).

Herrera et al., "TGF β–induced Growth Inhibition in Primary Fibroblasts Requires the Retinoblastoma Protein," *Mol. Biol. Cell.* 7(9):1335–1342 (1996).

Heuman et al., "Conjugates of Ursodeoxycholate Protect Against Cholestasis and Hepatocellular Necrosis Caused by More Hydrophobic Bile Salts," *Gastroenterology*, 100(1):203–211 (1991).

Heuman et al., "Conjugates of Ursodeoxycholate Protect Against Cytotoxicity of More Hydrophobic Bile Salts: In Vitro Studies in Rat Hepatocytes and Human Erythrocytes," *Hepatology*, 14(5):920–926 (1991).

Heuman et al., "Ursodeoxycholate Conjugates Protect Against Disruption of Cholesterol–Rich Membranes by Bile Salts," *Gastroenterology*, 106(5):1333–1341 (1994).

Hirano et al., "Induction of the transcription factor AP–1 in cultured human colon adenocarcinoma cells following exposure to bile acids," *Carcinogenesis*, 17(3):427–433 (1996).

Jacobson et al., "Programmed cell death and Bcl–2 protection in the absence of a nucleus," *EMBO J.*, 13(8):1899–1910 (1994).

Jänicke et al., "Specific cleavage of the retinoblastoma protein by an ICE–like protease in apoptosis," *EMBO J.*, 15(24):6969–6978 (1996).

Jones et al., "Bile Salt–Induced Hepatocyte Apoptosis Involves Activation of Protein Kinase C," Abstract, *Gastroenterology*, 110(4 Suppl.):A1224 (1996).

Jones et al., "PKC Contributes to Bile Salt–Induced Apoptosis of Hepatocytes," Abstract 2946, *FASEB Journal*, 11(3):A509 (1997).

Jones et al., "Bile salt–induced apoptosis of hepatocytes involves activation of protein kinase C," *Am. J. Physiol.*, 272(5):G1109–G1115 (May, 1997).

Kandell et al., "Bile Salt/Acid Induction of DNA Damage in Bacterial and Mammalian Cells: Implications for Colon Cancer," *Nutr. Cancer*, 16(3&4):227–238 (1991).

Koga et al., "Nuclear DNA Fragmentation and Expression of Bcl–2 in Primary Biliary Cirrhosis," *Hepatology*, 25(5):1077–1084 (May 1997).

Kren et al., "Differential Regulation of Multiple Gap Junction Transcripts and Proteins during Rat Liver Regeneration," *J. Cell Biol.*, 123(1):707–718 (1993).

Kren et al., "Posttranscriptional regulation of mRNA levels in rat liver associated with deoxycholic acid feeding," *Am. J. Physiol.*, 269(6):G961–G973 (1995).

Kroemer et al., "The biochemistry of programmed cell death," *FASEB J.*, 9:1277–1287 (1995).

Kurosawa et al., "Hepatocytes in the bile duct–ligated rat express Bcl–2," *Am. J.Physiol.*, 272(6):G1587–G1593 (Jun. 1997).

Kwo et al., "Ursodeoxycholate and its Conjugates Protect Against Glycodeoxycholate–Induced Apoptosis," Abstract 640, *Hepatology*, 20(4 Part 2):256A (1994).

Kwo et al., "Nuclear serine protease activity contributes to bile acid–induced apoptosis in hepatocytes," *Am. J. Physiol.*, 268(4):G613–G621 (1995).

LaRusso et al., "Coordinate Secretion of Acid Hydrolases in Rat Bile; Hepatocyte Exocytosis of Lysosomal Protein?" *J. Clin. Invest.*, 64:948–954 (1979).

Lawson et al., "Chapter 5: Mass Spectrometry of Bile Acids," *The Bile Acids, Chemistry, Physiology, and Metabolism, vol. 4: Methods and Applications*, Setchell et al., eds., Plenum Press, New York, Title page, publication page, table of contents, and pp. 167–267 (1988).

Lindor et al., "The Combination of Ursodeoxycholic Acid (UDCA) and Methotrexate (MTX) for Patients with Primary Biliary Cirrhosis (PBC): The Results of a Pilot Study," Abstract 421, *Hepatology*, 20(1 Part 2):202A (1994).

Mariash et al., "Rapid Synergistic Interaction between Thyroid Hormone and Carbohydrate on $mRNA_{S14}$ Induction," *J. Biol. Chem.*, 261(12):9583–9586 (1986).

Nagata et al., "The Fas Death Factor," *Science*, 267(5203):1449–1456 (1995).

Nishigaki et al., "Ursodeoxycholic Acid Corrects Defective Natural Killer Activity by Inhibiting Prostaglandin $E_2$ Production in Primary Biliary Cirrhosis," *Dig. Dis. Sciences*, 41(7):1487–1493 (1996).

Oberhammer et al., "Induction of apoptosis in cultured hepatocytes and in regressing liver by transforming growth factor β1," *Proc. Natl. Acad. Sci. USA*, 89(9):5408–5412 (1992).

Ogasawara et al., "Lethal effect of the anti–Fas antibody in mice," *Nature*, 364(6440):806–809 (1993).

Pastorino et al., "Cyclosporin and Carnitine Prevent the Anoxic Death of Cultured Hepatocytes by Inhibiting the Mitochondrial Permeability Transition," *J. Biol. Chem.*, 268(19):13791–13798 (1993).

Patel et al., "Increases of Intracellular Magnesium Promote Glycodeoxycholate–induced Apoptosis in Rat Hepatocytes," *J. Clin. Invest.*, 94(6):2183–2192 (1994).

Patel et al., "Hepatocyte Apoptosis Induced by Glycodeoxycholate is Mediated By a Rise in Cytosolic Free Magnesium," Abstract, *Gastroenterology*, 106(4 Suppl.):A958 (1994).

Patel et al., "Inhibition of Bile Salt Induced Hepatocyte Apoptosis by the Novel Antioxidant Lazaroid U83836E," Abstract 2422, *FASEB J.*, 9(3):A418 (1995).

Patel et al., "Apoptosis and Hepatobiliary Disease," *Hepatology*, 21(5):1725–1741 (1995).

Patel et al., "The role of proteases during apoptosis," *FASEB J.*, 10(5):587–597 (1996).

Patel et al., "Inhibition of Bile–Salt–Induced Hepatocyte Apoptosis by the Antioxidant Lazaroid U83836E," *Toxicol. Appl. Pharmacol.*, 142(1):116–122 (Jan. 1997).

Podda et al., "Effects of Ursodeoxycholic Acid and Taurine on Serum Liver Enzymes and Bile Acids in Chronic Hepatitis," *Gastroenterology*, 98(4):1044–1050 (1990).

Poupon et al., "Ursodiol for the Long–term Treatment of Primary Biliary Cirrhosis," *N. Engl. J. Med.*, 330(19):1342–1347 (1994).

Promega, "Apoptosis Detection Systems from Promega," *Bench Press*, Promega Newsletter, Issue 4, 1 page (Oct. 1998).

Quist et al., "Activation of Mast Cells by Bile Acids," *Gastroenterology*, 101(2):446–456 (1991).

Reed, "Double identity for proteins of the Bcl–2 family," *Nature*, 387(6635):773–776 (Jun. 1997).

Roberts et al., "Purification and Characterization of the Novel Nuclear Serine Protease Mediating Bile Salt–Induced Apoptosis of Hepatocytes," Abstract, *Gastroenterology*, 110(4 Suppl.):A1305 (1996).

Roberts et al., "Translocation of cathepsin B from the cytoplasm to the nucleus contributes to bile salt–induced hepatocyte apoptosis," Abstract 508, 47th Ann. Meeting, Am. Assoc. for the Study of Liver Diseases, Nov. 8–12, *Hepatology*, 24(4 Part 2):253A (1996).

Rodrigues et al., "A Novel Role for Ursodeoxycholic Acid in Modulating Apoptosis in Rat Liver, Isolated Rat Hepatocytes, and Human Hepatoma Cells," Nov. 7–11, 17 pages (Nov. 1997).

Rodrigues et al., "Ursodeoxycholic Acid May Inhibit Deoxycholic Acid–Induced Apoptosis by Modulating Mitochondrial Transmembrane Potential and Reactive Oxygen Species Production," *Mol. Med.*, 4(3):165–178 (Mar. 1998).

Rodrigues et al., "A Novel Role for Ursodeoxycholic Acid in Inhibiting Apoptosis by Modulating Mitochondrial Membrane Perturbation," *J. Clin. Invest.*, 101(12):2790–2799 (Jun. 15, 1998).

Rodrigues et al., "Ursodeoxycholic acid prevents cytochrome c release in apoptosis by inhibiting mitochondrial membrane depolarization and channel formation," *Cell Death Differ.*, 6(9):842–854 (Sep. 1999).

Schulze–Osthoff et al., "Cell Nucleus and DNA Fragmentation Are Not Required for Apoptosis," *J. Cell Biol.*, 127(1):15–20 (1994).

Schmucker et al., "Hepatic Injury Induced by Bile Salts: Correlation Between Biochemical and Morphological Events," *Hepatology*, 12(5):1216–1221 (1990).

Setchell et al., "Metabolism of orally administered tauroursodeoxycholic acid in patients with primary biliary cirrhosis," *Gut*, 38(3):439–446 (1996).

Setchell et al., "Bile Acid Concentrations in Human and Rat Liver Tissue and in Hepatocyte Nuclei," *Gasroenterology*, 112(1):226–235 (Jan. 1997).

Silva et al., "Bilrubin–Induced Apoptosis in Asrocytes is Prevented By Ursodeoxycholic Acid," Abstract, American Assn. for the Study of Liver Diseases, Nov. 4–10, Chicago (Nov. 1998).

Sokol et al., "Oxidant Injury to Hepatic Mitochondrial Lipids in Rats With Dietary Copper Overload," *Gastroenterology*, 99(4):1061–1071 (1990).

Sokol et al., "Evidence for Involvement of Oxygen Free Radicals in Bile Acid Toxicity to Isolate Rat Hepatocytes," *Hepatology*, 17(5):869–881 (1993).

Spivey et al., "Tauroursodeoxycholate Prevents Glycochenodeoxycholate Induced Nonlysosomal Proteolysis and Cytotoxicity in Isolated Rat Hepatocytes," Abstract 445, *Hepatology*, 16(4 Part 2):156A (1992).

Spivey et al., "Glycochenodeoxycholate–induced Lethal Hepatocellular Injury in Rat Hepatocytes," *J. Clin. Invest.* 92(1):17–24 (1993).

Stefaniwsky et al., "Ursodeoxycholic Acid Treatment of Bile Reflux Gastritis," *Gastroenterology*, 89(5):1000–1004 (1985).

Suchy, "Hepatocellular Transport of Bile Acids," *Sem. Liver Dis.*, 13(3):235–247 (1993).

Thompson, "Apoptosis in the Pathogenesis and Treatment of Disease," *Science*, 267(5203):1456–1462 (1995).

Trembley et al., "Differential Regulation of Cyclin B1 RNA and Protein Expression during Hepatocyte Growth in Vivo," *Cell Growth Differ.*, 7(7):903–916 (1996).

Walajtys–Rhode et al., "The Role of the Matrix Calcium Level in the Enhancement of Mitochondrial Pyruvate Carboxylation by Glucagon Pretreatment," *J. Biol. Chem.*, 267(1):370–379 (1992).

Walker et al., "Detection of the Initial Stages of DNA Fragmentation in Apoptosis," *Bio Techniques*, 15(6):1032–1040 (1993).

Wyllie et al., "Cell Death: The Significance of Apoptosis," *Int. Rev. Cytol.*, 68:251–306 (1980).

Yang et al., "Bad, a Heterodimeric Partner for Bcl–$x_L$, and Bcl–2, Displaces Bax and Promotes Cell Death," *Cell*, 80(2):285–291 (1995).

Yoshikawa et al., "Immunomodulatory Effects of Urosodeoxycholic Acid on Immune Responses," *Hepatology*, 16(2):358–364 (1992).

Zamzami et al., "Reduction in Mitochondrial Potential Constitutes an Early Irreversible Step of Programmed Lymphocyte Death in Vivo," *J. Exp. Med.*, 181(5):1661–1672 (1995).

\* cited by examiner

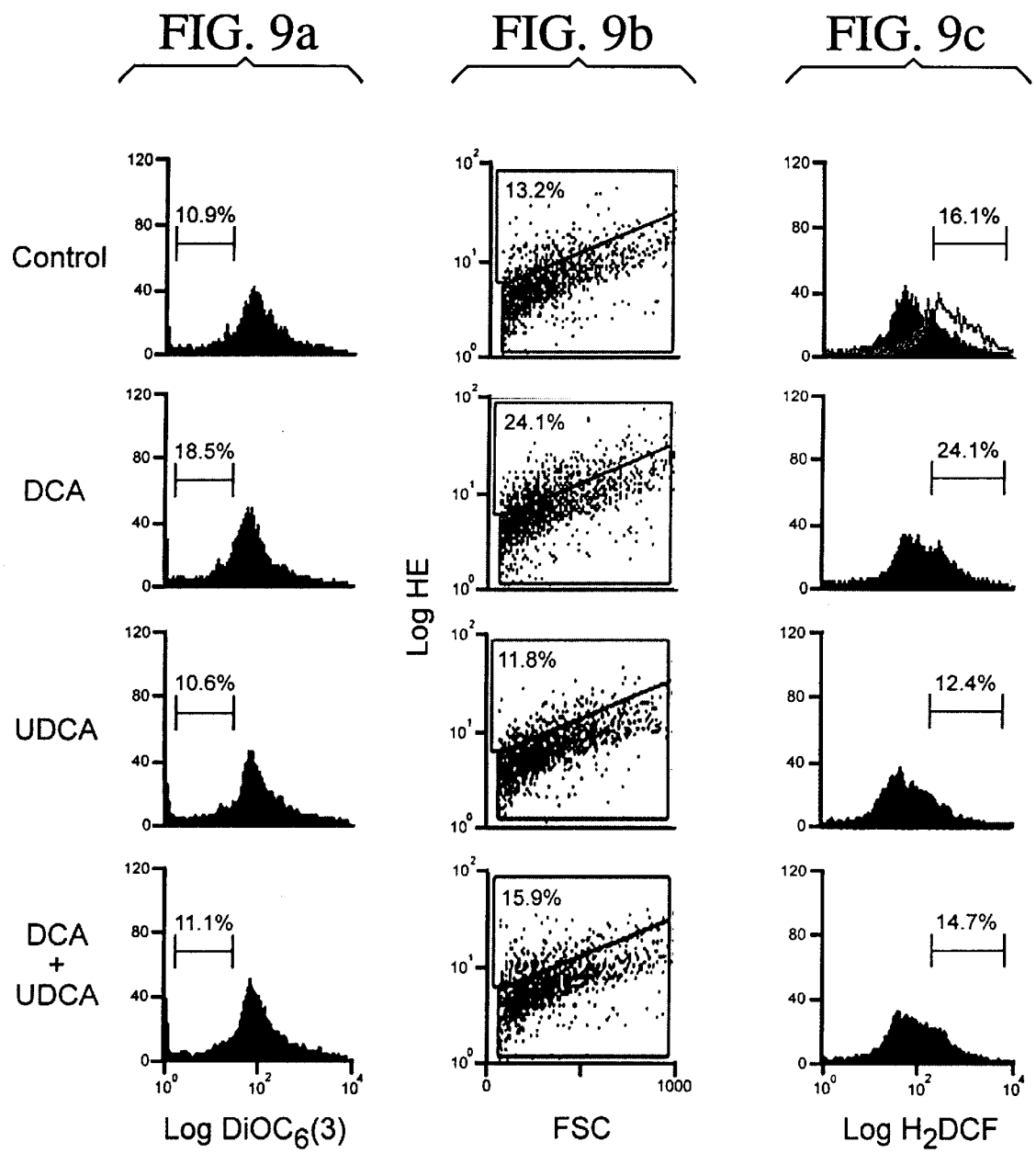

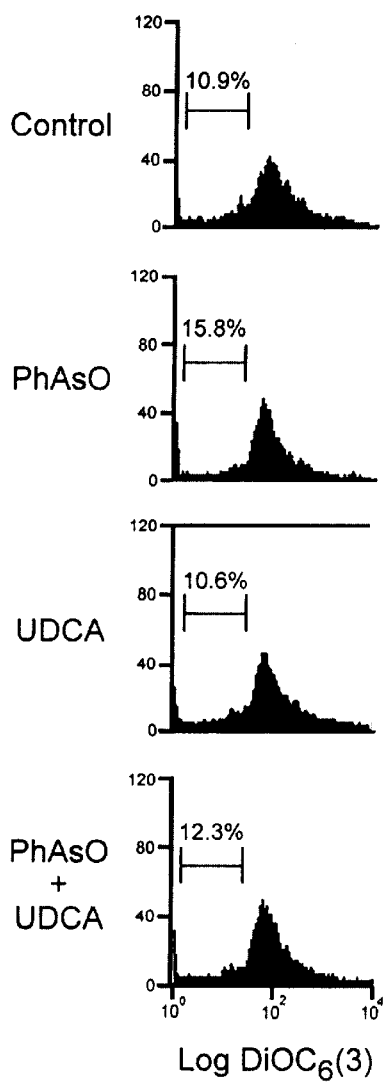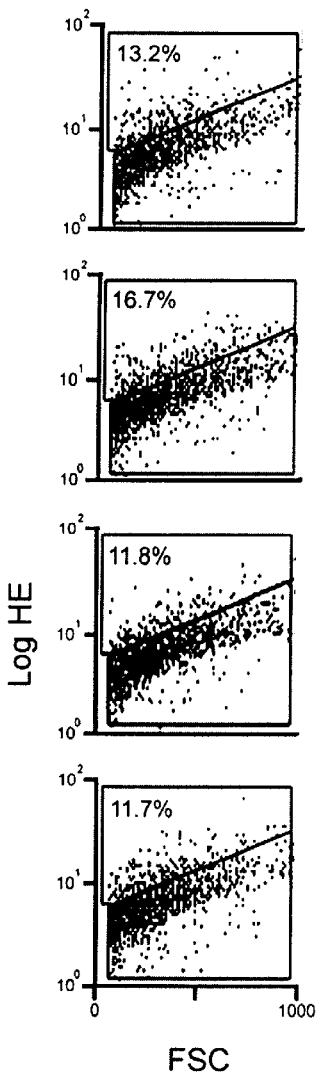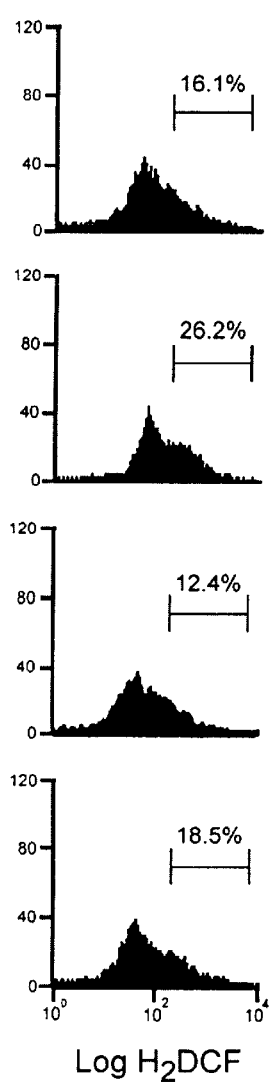

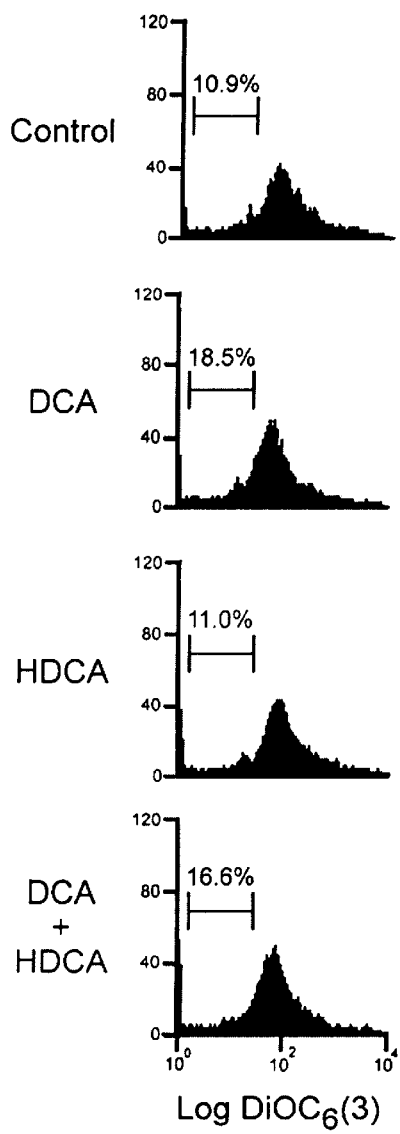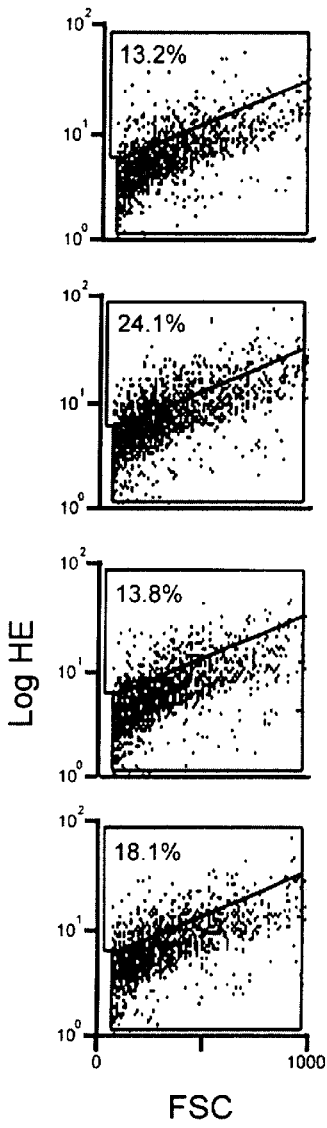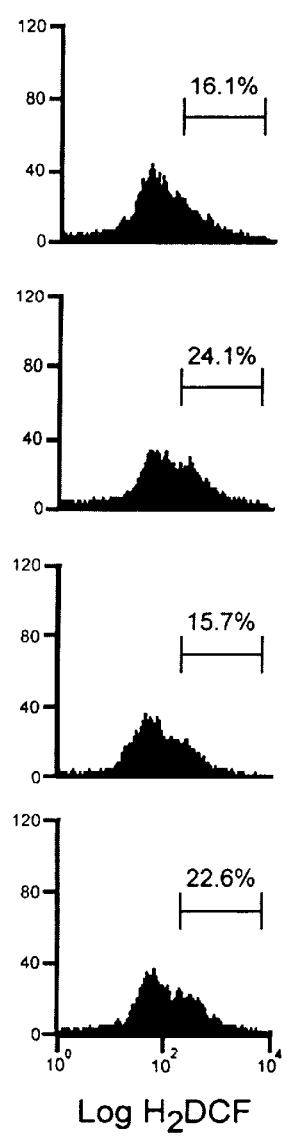

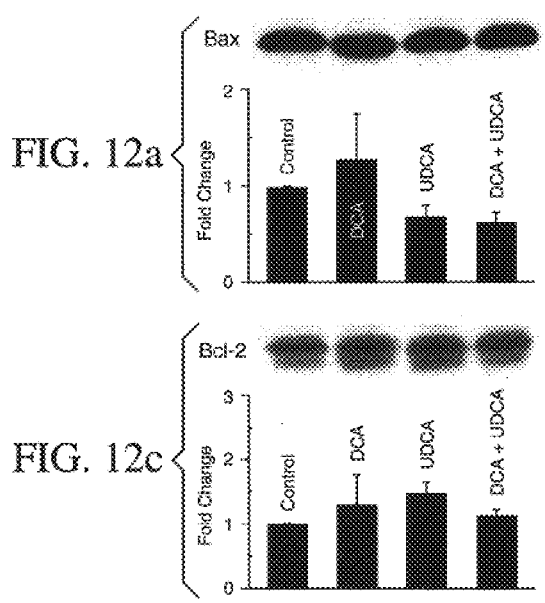
FIG. 12a
FIG. 12c
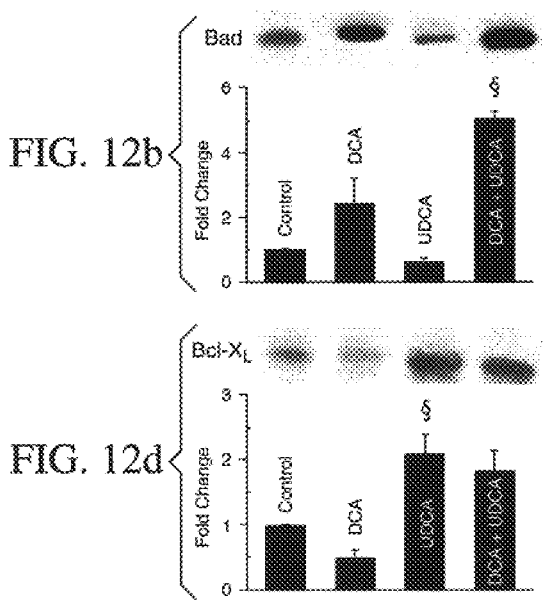
FIG. 12b
FIG. 12d

METHODS OF LIMITING APOPTOSIS OF CELLS

CROSS-REFERENCE TO RELATED APPLICATIONS

The present application claims priority to U.S. Provisional Patent Application Ser. No. 60/060,040, filed on Sep. 25, 1997, which is incorporated herein by reference.

BACKGROUND OF THE INVENTION

Accumulation of bile acids within the hepatocyte is thought to play a key role in liver injury during cholestasis. Although the initial insult in certain hepatobiliary diseases such as primary biliary cirrhosis may be immunological, cell injury is probably exacerbated by direct chemical damage from the hydrophobic bile acids. Although the cytotoxicity of hydrophobic bile acids to hepatocytes and a variety of other cell types has been attributed to the membrane disruptive effects from their detergent properties, it is now apparent that nondetergent mechanisms are also involved. In contrast, hydrophilic bile acids such as ursodeoxycholic acid (UDCA) and its taurine and glycine conjugates appear to protect against cholestasis and the toxicity induced by the hydrophobic bile acids (Heuman et al., *Gastroenterology*, 100, 203–211 (1991) and Heuman et al., *Gastroenterology*, 106, 1333–1341(1994)). Although the mechanism of action is not entirely understood, the oral administration of UDCA markedly improves clinical and biochemical indices in some chronic liver diseases (Podda et al., *Gastroenterology*, 98, 1044–1050 (1990); Chazouilleres et al., *J. Hepatology*, 11, 120–123 (1990); and Poupon et al., *N. Engl. J. Med.*, 330, 1342–1347 (1994)). This protective effect appears to result from mechanisms beyond simply displacing toxic bile acids from the liver.

Bile acid-induced toxicity is typically characterized by hepatocyte swelling, disruption of membrane plasma integrity, and release of intracellular constituents. As a consequence, liver cell death has been characterized as loss of hepatocellular function associated with necrosis. Widespread hepatocyte necrosis, however, is not a prominent feature in most cholestatic liver diseases. In fact, it now appears that hepatocyte cell death occurs more commonly by apoptosis than necrosis (Columbano et al., *J. Cell. Biochem.*, 58, 181–190 (1995)). Apoptosis, or programmed cell death, is characterized by distinctive morphologic and biochemical changes including cell shrinkage, loss of intercellular membrane contact, progressive condensation of chromatin and cytoplasm, and subsequent nuclear fragmentation. These events culminate in the characteristic formation of apoptotic bodies, consisting of nuclear fragments and intact cell organelles surrounded by plasma membrane. The internucleosomal degradation of DNA, which results in fragmentation in multiples of 180 base pairs, and the consequent appearance of a characteristic DNA ladder by gel electrophoresis has become an identifying feature of apoptosis at the molecular level.

Hydrophobic bile salts such as glycodeoxycholate and glycochenodeoxycholate directly induce apoptosis in isolated rat hepatocytes (Spivey et al., *J. Clin. Invest.* 92 17–24 (1993) and Patel et al., *J. Clin. Invest.*, 94, 2183–2192 (1994)). Moreover, it has been reported that bile salt induced apoptosis of hepatocytes involves activation of the protease cathepsin B through the protein kinase C-dependent pathway (Jones et al., *Am. J. Physiol.*, 272 G1109–G1115 (1997)). Features of apoptosis have been observed in several types of liver diseases. In fact, it was recently reported that nuclear DNA fragmentation and de novo Bcl-1-2 expression were increased in primary biliary cirrhosis, and significantly inhibited in patients treated with UDCA (Koga et al., *Hepatology*, 25, 1077–1084 (1997)). Although the precise molecular mechanism of cytoprotection by UDCA is not completely known, it has been shown that ursodeoxycholate reduces the mitochondrial membrane damage from certain hydrophobic bile acids (Botla et al., *J. Pharmacol. Exp. Ther.*, 272, 930–938 (1995)). In fact, the results suggested a physiochemical explanation for the bioenergetic form of cell injury associated with hydrophobic bile salts. UDCA cytoprotection may, in part, be due to inhibition of bile salt-induced mitochondrial membrane permeability. It is now apparent that disruption of mitochondrial function is a key factor in the genesis of apoptosis (Reed et al., *Nature (Lond.).*, 387, 773–776 (1997)). This is supported by the observation that the cell nucleus and DNA fragmentation may not be required for cells to undergo apoptosis.

There are a number of agents other than hydrophobic bile acids that induce apoptosis. Furthermore, there are a number of mechanisms by which apoptosis is induced. Examples of such agents include TGF-β1, anti-Fas antibody, okadaic acid, and ethanol. Thus, there is a need for agents that are inhibitory to such inducers of apoptosis which are unrelated to hydrophobic bile acids.

SUMMARY OF THE INVENTION

The present invention provides a method for limiting apoptosis (i.e., programmed cell death) of a mammalian cell population. The method comprises contacting the cell population with an effective amount of ursodeoxycholic acid, a salt thereof, an analog thereof, or a combination thereof, wherein the apoptosis is induced by a nonmembrane damaging agent, such as TGF-β1, anti-Fas antibody, or okadaic acid. The cell population can include, for example, hepatocytes and astrocytes. The contacting step can be performed in vitro, in vivo, and a combination thereof. As used herein, "in vitro" is to be distinguished from "in vivo." In vitro refers to an artificial environment location of the cell population to be treated, such as a cell culture in a tissue culture dish. In vivo refers to a natural environment location of the cell population to be treated, such as in a mammalian body. Preferably, the cell population is a human cell population, and the contacting step involves administering an effective amount of ursodeoxycholic acid, a salt thereof, an analog thereof, or a combination thereof.

One aspect of the present invention provides a method that includes a step of administering to a patient an effective amount of ursodeoxycholic acid, a salt thereof, an analog thereof (e.g., glyco- and tauro-), or a combination thereof. Preferably, the step of administering comprises administering parenterally or intravenously.

The present invention also provides a method for limiting apoptosis of a mammalian cell population, the method comprising contacting the cell population with an effective amount of ursodeoxycholic acid, a salt thereof, an analog thereof, or a combination thereof, wherein the apoptosis is induced by ethanol.

Another aspect of the present invention is a method for limiting apoptosis of a human cell population. Preferably, the method includes contacting the cell population with an effective amount of a hydrophilic bile acid, a salt thereof, an analog thereof, or a combination thereof, wherein the apoptosis is induced by a hydrophobic bile acid.

Yet another aspect of the invention is a method for limiting apoptosis of a mammalian cell population, wherein the method includes contacting the cell population with an effective amount of a hydrophilic bile acid, a salt thereof, an analog thereof, or a combination thereof, wherein the apoptosis is induced by TGF-β1, anti-Fas antibody, or okadaic acid.

Still another aspect of the present invention is a method for inhibiting apoptosis associated with a nonliver disease in vivo, the method including administering ursodeoxycholic acid, a salt thereof, an analog thereof, or a combination thereof. The nonliver disease can be an autoimmune disease, a cardio-/cerebrovascular disease (e.g., stroke, myocardial infarction, and the like), or a neurodegenerative disease, for example.

The present invention also provides a method of reducing expression of c-myc in a cell, the method comprising contacting the cell with an effective amount of ursodeoxycholic acid, salts thereof, or analogs thereof.

Yet another method of involves increasing levels of Bcl-$X_L$ in a cell, the method comprising contacting the cell with an effective amount of ursodeoxycholic acid, salts thereof, or analogs thereof.

The present invention also provides a method of inhibiting Bax translocation from the cytoplasm of a cell to a mitochondrial membrane. This is believed to result in the inhibition of changes in the mitochondrion. The method includes a step of contacting the cell with an effective amount of ursodeoxycholic acid, a salt thereof, an analog thereof, or a combination thereof.

A further aspect of the present invention provides a method for limiting apoptosis of a mammalian cell population, the method comprising contacting the cell population with an effective amount of an apoptotic limiting compound selected from the group of ursodeoxycholic acid, a salt thereof, an analog thereof, and a combination thereof, wherein the apoptosis is induced by a membrane damaging agent selected from the group consisting of unconjugated bilirubin, conjugated bilirubin, and a combination thereof.

As mentioned above, the cell population can be hepatocytes, astrocytes, and the like. The contacting step can occur in vitro, in vivo, and a combination thereof. In one embodiment, the cell population is a human cell population.

Preferably, the step of contacting comprises administering to a patient an effective amount of an apoptotic limiting compound selected from the group of ursodeoxycholic acid, a salt thereof, an analog thereof, and a combination thereof In accordance with the present invention, the apoptotic limiting compound can be administered in combination with a pharmaceutically acceptable carrier. Alternatively, administering the apoptotic limiting compound can be administered parenterally. In another embodiment, administering the apoptotic limiting compound can be administered orally.

BRIEF DESCRIPTION OF THE DRAWINGS

(FIG. 1A) Hepatocytes were incubated with 50 μM of either DCA, UDCA, DCA+UDCA, or no bile acid addition (control) in William's E medium supplemented with 10% FBS and fixed for morphological analysis. Cells were fixed and stained with 5 μg/ml Hoechst 33258 to detect nuclear fragmentation and condensed chromatin. The percent apoptosis was determined after treatment with bile acids for 2 h, 4 h, and 6 h.

FIG. 7. Mitochondrial membrane permeability transition (abbreviated herein as MPT) changes in isolated rat liver mitochondria incubated with bile acids. Mitochondria were isolated and incubated (1 mg protein/ml) with either DCA, UDCA, DCA+UDCA, or no bile acid (control) in respiration buffer.

FIG. 8. Dose-response of isolated mitochondria to bile acid-induced MPT. Mitochondria were isolated and incubated (1 mg protein/ml) with either DCA, DCA+UDCA, PhAsO, PhAsO+UDCA, HDCA, or DCA+HDCA in respiration buffer. Percent change in MPT was measured by monitoring mitochondrial swelling.

FIG. 9. Reduction of $\Delta\Psi_m$ and increased production of ROS after incubation of isolated mitochondria with DCA. Isolated mitochondria were incubated with 100 µM DCA, 500 µM UDCA, 100 µM DCA+500 µM UDCA, or no bile acid addition (control) for 5 min. In the coincubation experiments, mitochondria were pretreated with UDCA alone for 5 min prior to addition of DCA. Isolated mitochondria (1 mg protein/ml) were suspended in respiration buffer and incubated for 15 min at 37° C. with 50 nM DiOC$_6$(3), 2 µM HE, or 5 µM H$_2$DCFDA and analyzed by cytofluorometry. The percentages reflect (FIG. 9A) the disruption in $\Delta\Psi_m$; (FIG. 9B) the increased production of superoxides; and (FIG. 9C) the increased production of peroxides during treatment with DCA, and the respective inhibition by UDCA. The treatment groups are indicated on the left; the open peak in the control group panel C shows a positive control after incubation with 10 mM H$_2$O$_2$. The data shown are representative of at least three different experiments. Coincubation with UDCA was associated with significant inhibition of mitochondrial perturbation $p<0.05$, or lower).

FIG. 10. Reduction of $\Delta\Psi_m$ and increased production of ROS after incubation of isolated mitochondria with PhAsO. Isolated mitochondria were incubated with 80 µM PhAsO, 500 µM UDCA, 80 µM PhAsO+500 µM UDCA, or no addition (control) for 5 min. In the coincubation experiments, mitochondria were pretreated with UDCA alone for 5 min prior to addition of PhAsO. Isolated mitochondria (1 mg protein/ml) were suspended in respiration buffer and incubated for 15 min at 37° C. with 50 nM DiOC$_6$(3), 2 µM HE, or 5 µM H$_2$DCFDA and analyzed by cytofluorometry. The percentages reflect (FIG. 10A) the disruption in $\Delta\Psi_m$; (FIG. 10B) the increased production of superoxides; and (FIG. 10C) the increased production of peroxides during treatment with PhAsO, and the respective inhibition by UDCA. The treatment groups are indicated on the left and the data shown are representative of at least three different experiments. Coincubation with UDCA was associated with significant inhibition of mitochondrial perturbation ($p<0.05$, or lower).

FIG. 11. HDCA does not significantly inhibit the DCA-induced reduction of $\Delta\Psi_m$ and increased production of ROS in isolated rat liver mitochondria. Isolated mitochondria were incubated with 100 µM DCA, 500 µM HDCA, 100 µM DCA+500 µM HDCA, or no bile acid addition (control) for 5 min. In the coincubation experiments, mitochondria were pretreated with 500 µM HDCA alone for 5 min prior to addition of DCA. Isolated mitochondria (1 mg protein/ml) were suspended in respiration buffer and incubated for 15 min at 37° C. with 50 nM DiOC$_6$(3), 2 µM HE, or 5 µM H$_2$DCFDA and analyzed by cytofluorometry. The percentages reflect (FIG. 11A) the disruption in $\Delta\Psi_m$; (FIG. 11B) the increased production of superoxides; and (FIG. 11C) the increased production of peroxides during treatment with DCA, and the absence of significant protection by HDCA. The data shown are representative of at least three different experiments and the treatment groups are indicated at left.

FIG. 12. Western blot analysis of apoptosis-associated proteins in liver from bile acid fed rats. Cytoplasmic proteins (150 µg/lane) from control, DCA, UDCA, and DCA+UDCA fed rats were isolated from whole liver. Following SDS-PAGE and transfer, the nitrocellulose membranes were incubated with antibodies to either Bax, Bad, Bcl-2 or Bcl-X$_L$ and the proteins were detected using ECL chemiluminescence. Representative western blots of cytoplasmic proteins are shown at top and the accompanying histograms below depict the mean changes±standard error of the mean (S.E.M.) in protein levels relative to control. The proteins are indicated on the left and the values shown are from at least three different animals from each group. [517] $p<0.001$ from Bad control; $p<0.05$ from Bcl-X$_L$ control.

DETAILED DESCRIPTION OF PREFERRED EMBODIMENTS

Figures 1A, 1B, 1C, 1D:
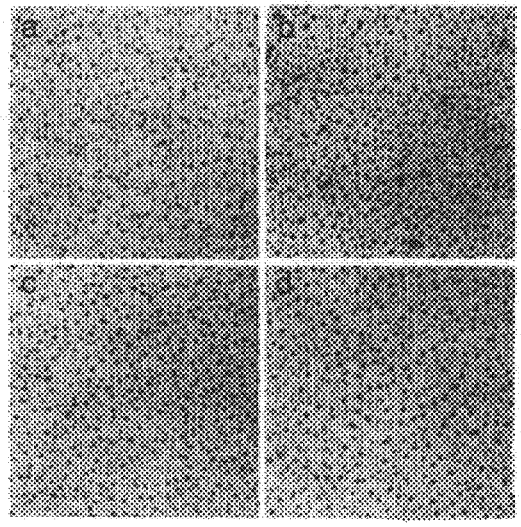
(FIG. 1A) TUNEL-positive hepatocytes (brown stain) in rats fed no bile acid (a); DCA (b); UDCA (c); and DCA+UDCA (d).
(FIG. 1B) Percent of TUNEL-positive hepatocytes. Values are means±standard deviations (S.D.) of at least three liver tissue cryosections from each animal group. Only DCA feeding was associated with a significant increase (*$P<0.001$) in TUNEL-positive cells.

The present invention provides methods that involve the modulation of the apoptotic threshold in hepatocytes and nonliver cells from agents acting through different apoptotic pathways. Significantly, the methods of the present invention limit the incidence of apoptosis in a cell population that is induced by deoxycholic acid (DCA), as well as ethanol, transforming growth factor (TGF)-β1, the Fas ligand (i.e., anti-Fas antibody), okadaic acid, and unconjugated bilirubin, for example. Each of these agents may act in a totally different mechanistic pathway, however, it has been discovered that hydrophilic bile acids such as ursodeoxycholic acid, salts thereof, and analogs thereof can effect (e.g., inhibit) their function with respect to apoptosis.

In certain embodiments, the methods of the present invention limit the incidence of apoptosis in a cell population that is induced by nonmembrane damaging agents, such as transforming growth factor (TGF)-β1, the Fas ligand (i.e., anti-Fas antibody), and okadaic acid, for example. These agents typically operate through signal transduction, whereas agents such as DCA and ethanol are believed to operate through damaging and/or infiltrating mitochondrial membranes, i.e., are considered membrane damaging agents also including unconjugated bilirubin, conjugated bilirubin, and a combination thereof.

As used herein, the terms "limit" or "limiting" in the context of the incidence of apoptosis refer to, for example, preventing, reducing, suppressing, and/or inhibiting the occurrence of apoptosis, which can be associated with a variety of diseases. As used herein, the terms "cells" or "cell population" refer to mammalian cells, particularly human cells. They can include, for example, isolated hepatocytes and hepatoma cells, as well as cells such as Saos-2 (a human sarcoma cell line), Cos-7 (a monkey kidney cell line), HeLa (a human cervical cancer cell line), and astrocytes (rat brain cells). The cells can be a human cell population or other mammalian cell population. The cells can be treated in a cell in vitro, in vivo, and a combination thereof.

For example, a method in accordance with the present invention conferred significant protection against apoptosis induced by TGF-β1 and okadaic acid in HuH-7 cells (human hepatoma cells), as well as HeLa and Cos-7 cells, whereas the Ohydrophilic bile acids hyodeoxycholic and taurocholic acids did not. Additionally, a reduction in apoptosis by UDCA was found to be similar to its inhibition of mitochondrial membrane perturbation. While not wishing to be bound by any particular theory, it is believed that an apoptotic mechanism common to these multiple inducing agents is specifically modulated by UDCA and its conjugated derivatives, and not simply by a detergent-sparing effect.

Rather, it suggests that at least one mechanism by which UDCA is able to inhibit apoptosis is prevention of mitochondrial dysfunction.

The methods of the present invention involve contacting such cells with a hydrophilic bile acid, salts thereof, analogs thereof, or combinations thereof. As used herein, hydrophilic bile acids are those more hydrophilic than deoxycholic acid (DCA). This can be determined by evaluating the partition coefficient between water and octanol, with the more hydrophilic bile acids being more favorable toward water. Alternatively, the more hydrophilic bile acids have earlier retention times on a reverse-phase column using high performance liquid chromatography. A particularly preferred hydrophilic bile acid includes ursodeoxycholic acid. Examples of analogs of hydrophilic bile acids include conjugated derivatives of bile acids. Two particularly preferred conjugated derivatives include glyco- and tauro-ursodeoxycholic acid.

Although all hydrophilic bile acids may not be useful in all methods of the present invention, they can be evaluated readily by a method similar to that mentioned above. In particular, primary hepatocytes can be incubated with TGF-β1 or okadaic acid and a compound to be evaluated for antiapoptotic activity. Effects can be evaluated by fluorescence microscopy of Hoechst-stained nuclei, as described herein. For example, hyodeoxycholic acid and taurocholic acid are hydrophilic bile acids, but they are not effective for all methods of the present invention. Furthermore, the glyco- and tauro- conjugates of deoxycholic acid are not effective for all methods of the present invention.

Such compounds are used in amounts effective to limit the incidence of apoptosis. Accordingly, they are referred to herein as "apoptosis limiting" or "apoptotic limiting" compounds. They can be used in the methods of the present invention in the form of a composition that also includes a pharmaceutically acceptable carrier, if so desired. Typically, for preferred embodiments, the apoptosis limiting compounds described herein are formulated in pharmaceutical compositions and then, in accordance with methods of the invention, administered to a mammal, such as a human patient, in a variety of forms adapted to the chosen route of administration. The formulations include those suitable for oral, rectal, vaginal, topical, nasal, ophthalmic or parental (including subcutaneous, intramuscular, intraperitoneal and intravenous) administration. Treatment can be prophylactic or, alternatively, can be initiated after known exposure to an offending agent. Accordingly, administration of the compounds can be performed before, during or after exposure or potential exposure to suspected or known apoptosis inducing agents.

The formulations may be conveniently presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into a desired formulation.

Formulations of the present invention suitable for oral administration may be presented as discrete units such as tablets, troches, capsules, lozenges, wafers, or cachets, each containing a predetermined amount of the apoptosis limiting compound as a powder, in granular form, incorporated within liposomes, or as a solution or suspension in an aqueous liquid or non-aqueous liquid such as a syrup, an elixir, an emulsion, or a draught. Such compositions and preparations should contain at least about 500 mg/day to about 1000 mg/day, or, alternatively stated, about 10 mg/kg body weight to about 15 mg/kg body weight. The amount of apoptosis limiting compound in such therapeutically useful compositions is such that the dosage level will be effective to prevent, reduce, inhibit, or suppress the development of programmed cell death in the subject.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The apoptosis limiting compound may be incorporated into sustained-release preparations and devices.

The apoptosis limiting compounds of the invention can be incorporated directly into the food of the mammal's diet, as an additive, supplement, or the like. Thus, the invention further provides a food product containing an apoptosis limiting compound of the invention. Any food is suitable for this purpose, although processed foods already in use as sources of nutritional supplementation or fortification, such as breads, cereals, milk, and the like, may be more convenient to use for this purpose.

Formulations suitable for parenteral administration conveniently comprise a sterile aqueous preparation of the apoptosis limiting compound, or dispersions of sterile powders comprising the apoptosis limiting compound, which are preferably isotonic with the blood of the recipient. Isotonic agents that can be included in the liquid preparation include sugars, buffers, and salts such as sodium chloride. Solutions of the apoptosis limiting compound can be prepared in water, optionally mixed with a nontoxic surfactant. Dispersions of the apoptosis limiting compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the apoptosis limiting compound, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the apoptosis limiting compounds over a prolonged period can be achieved by including agents for delaying, for example, aluminum monostearate and gelatin.

Nasal spray formulations comprise purified aqueous solutions of the apoptosis limiting compound with preservative agents and isotonic agents. Such formulations are preferably adjusted to a pH and isotonic state compatible with the nasal mucous membranes. Ophthalmic formulations are prepared by a similar method to the nasal spray, except that the pH and isotonic factors are preferably adjusted to match that of the eye. Formulations for rectal or vaginal administration may be presented as a suppository with a suitable carrier such as cocoa butter, or hydrogenated fats or hydrogenated fatty carboxylic acids.

Topical formulations comprise the apoptosis limiting compound dissolved or suspended in one or more media such as mineral oil, petroleum, polyhydroxy alcohols or other bases used for topical pharmaceutical formulations. Examples of such formulations include cosmetic lotion, creme, or sunscreen for use on the skin.

In addition to the aforementioned ingredients, the formulations of this invention may further include one or more accessory ingredients including diluents, buffers, binders, disintegrants, surface active agents, thickeners, lubricants, preservatives (including antioxidants) and the like.

Useful dosages of the apoptosis limiting compounds described herein can be determined by comparing their in vitro activity and the in vivo activity in animals models. Methods for extrapolation of effective dosages in mice, and other animals, to humans are known in the art.

Generally, for adult humans, single dosages for injection, infusion, or ingestion will generally vary from about 500 mg to about 1000 mg (i.e., a dosage of about 10 mg to about 15 mg per kg of body weight per day). It may be administered, for example, about 1 to about 3 times per day, to yield levels of about 10 to about 15 $\mu$mol per liter of serum.

In the following examples, DNA fragmentation and morphologic changes of apoptosis were determined by TUNEL assay and by nuclear staining, respectively. DCA treatment in vivo and in isolated hepatocytes resulted in about a 40-fold increase in apoptosis (P<0.001). Apoptosis in isolated rat hepatocytes increased 12-fold after incubation with 0.5% ethanol (P<0.001). HuH-7 cells underwent significant apoptosis with 1 nM TGF-$\beta$1 (P<0.001) or DCA at 100 $\mu$M (P<0.001). Hep G2 cells exhibited significant apoptosis after incubation with anti-Fas antibody (P<0.001). Finally, incubation with okadaic acid induced>30% apoptosis in both HuH-7 and Saos-2 cells. Coadministration of UDCA with each of the apoptosis-inducing agents was associated with a 50–100% inhibition of apoptotic changes (P<0.001) in all the cell types. UDCA fed rats exhibited significant hepatic changes in expression of the apoptosis-related proteins for Bad, Bax and BCl-$X_L$. UDCA was>20-fold more concentrated in the nuclei of livers from control and DCA fed rats than cytoplasmic levels (P<0.001), and comprised 91.4% of the total nuclear bile acid (BA) concentration with UDCA feeding. The results suggest that UDCA plays a central role in regulating the apoptotic threshold in both hepatocytes and nonliver cells, and may do so, in part, by modulating the expression of certain apoptosis-related genes.

Neurons may also die from apoptosis, particularly in oxygen-deprived brains. When brain ischemia was induced in laboratory animals by temporarily cutting the blood flow to the brain, several features of apoptosis were found in dying neurons. Preliminary results in a rat model indicate an improvement in mitochondria viability following a stroke injury in rats treated with tauroursodeoxycholic acid (TUDC). As compared to control animals, pretreatment with TUDC decreased the area of stroke damage by up to about 50%. These results indicate that ursodeoxycholic acid and its conjugated derivatives may provide benefit in rescuing injured cells following stroke injury.

Further, nerve cell injury from unconjugated bilirubin (UCB) may play a role in brain damage during neonatal hyperbilirubinemia. UCB treatment of astrocytes demonstrated a concentration and time dependent decrease in cell viability. For example, after 4 hours of incubation, apoptosis was increased about 6- and about 11 - fold over control values in the presence of 17 $\mu$M and 85.5 $\mu$M UCB, respectively. The percentage of apoptotic cells increased up to about 48% after incubation of astrocytes in 85.5 $\mu$M UCB for 22 hours. Coincubation with UDCA led to a decrease of over about 50% inhibition of apoptosis.

Advantages of the invention are illustrated by the following examples. However, the particular materials and amounts thereof recited in these examples, as well as other conditions and details, are to be interpreted to apply broadly in the art and should not be construed to unduly limit the invention.

EXAMPLES

Example I

A Novel Role for Ursodeoxycholic Acid in Inhibiting Apoptosis by Modulating Mitochondrial Membrane Perturbation A. Materials and Methods Animals and diets. Male 160–175 gram (g) Sprague-Dawley rats (Sprague-Dawley, Indianapolis, Ind.) were maintained on a 12-hour (h) light-dark cycle and fed standard laboratory chow ad libitum for 3 days. The animals were then transferred to metabolic cages and fed diets of standard laboratory chow supplemented with either no bile acid or 0.4% (wt/wt) DCA, UDCA, or a combination of DCA+UDCA (Bio-Serv, Frenchtown, N.J.). On day 10, the animals were sacrificed by exsanguination under ether anesthesia between 9 a.m. and 11 a.m. The livers were removed, rinsed in normal saline, and flash-frozen in liquid nitrogen. Liver tissue samples were embedded in OCT, and 5 $\mu$m-thick cryostat sections were cut and mounted on slides. At least three cryosections from three different animals in each group were fixed in 10% formalin in PBS, pH 7.4 for 10 minutes (min) at room temperature, washed with PBS, pH 7.4, and then incubated in ice-cold ethanol:acetic acid (2:1) at $-20°$ C. for a minimum of 5 min. All animals received human care in compliance with the Guide for the Care and use of Laboratory Animals, prepared by the National Academy of Sciences (NIH Publication No. 86–23, revised 1985).

Terminal transferase-mediated dUTP-digoxigenin nick end labeling (TUNEL) assay. Digoxigenin-nucleotide residues were added to 3'-OH ends of double or single-stranded DNA by terminal deoxynucleotidyl transferase. Reactions were performed according to the manufacturer's recommendations (Oncor, Inc., Gaithersburg, Md.), and the specimens were then coversliped with Permount medium (Fischer Scientific, Inc., Itasca, Ill.) prior to analysis by phase-contrast microscopy using a Nikon microscope (Nikon, Inc., Melville, N.Y.). Photographs were taken using Kodak Ektar-1000 film (Eastman Kodak Co., Rochester, N.Y.).

Cell culture and preparation of rat primary hepatocytes. Rat primary hepatocytes were isolated from male Sprague-Dawley rats (200–250 g) by collagenase perfusion as described previously (Mariash et al., *J. Biol. Chem.*, 261, 9583–9586 (1986)). Briefly, rats were aneshtesized with phenobarbitol and the livers were perfused with 0.05% collagenase. Hepatocyte suspensions were obained by passing digested livers through 0.125 mm gauze and washing cells in modified Eagles' medium (MEM, Life Technologies, Inc., Grand Island, N.Y.). Cell viability was determined by trypan blue exclusion and was typically 85 to 90%. After isolation, hepatocytes were resuspended in William's E medium (Life Technologies, Inc., Grand Island, N.Y.) supplemented with 26 mM sodium bicarbonate, 23 mM HEPES, 0.01 U/ml insulin, 2 mM L-glutamine, 10 nM dexamethasone, 5.5 mM glucose, 100 U/ml penicillin and 100 U/ml streptomycin and then $1.0 \times 10^6$ cells were plated on 35×10 mm PRIMARIA tissue culture dishes (Becton Dickinson Labware, Lincoln Park, N.J.). The cells were maintained at 37° C. in a humidified atmosphere of 5% $CO_2$ for 3 h. Plates were then washed with medium to remove dead cells, and medium containing 10% heat-inactivated FBS (55° C. for 30 min) was added (Atlanta Biologicals, Inc., Norcross, Ga.). Aliquots of $1.0 \times 10^5$ human (HuH-7) hepatoma cells were plated on 35×10 mm tissue culture dishes (Becton Dickinson Labware) and aintained at 37° C. in Dulbecco's MEM (Atlanta Biologicals, Inc.) supplemented with 10% FBS, 100 U/ml penicillin and 100 u/ml streptomycin for 3 h prior to incubation with bile acids.

Incubation of cells with bile acids. Freshly isolated rat hepatocytes were cultured for 3 h as described above and then incubated with William's E medium supplemented with either 50 $\mu$M DCA, 50 $\mu$M UDCA (Sigma Chemical Co., St. Louis, Mo.), their combination, or no bile acid (control), for 2 h, 4 h, and 6 h. HuH-7 cells cultured for 3 h as described above were incubated with Dulbecco's MEM medium supplemented with either 50 $\mu$M, 100 $\mu$M, 500 $\mu$M, or 1000 $\mu$M DCA, UDCA, DCA+UDCA, or no addition (control) for 6 h and 24 h. The medium was gently removed at the indicated time points and scored for nonviable cells by trypan blue dye exclusion. The attached cells were fixed for morphologic assessment of apoptotic changes.

In parallel experiments, isolated rat hepatocytes ($2 \times 10^7$ cells) and HuH-7 cells ($2 \times 10^6$ cells) were incubated with 50 $\mu$M or 100 M, respectively, of DCA, UDCA or DCA+UDCA for 6 h. Cells were washed 3 times with PBS, pH 7.4, harvested, centrifuged at 800×g for 5 min in a JS-4.0 Beckman rotor (Beckman Instruments, Inc., Schaumburg, Ill.) at 4° C., washed again, and the final pellet was flash-frozen in liquid nitrogen. Cells were then analyzed for intracellular bile acid concentrations by gas chromatography.

Bile acid quantification by gas chromatography. Individual bile acids were measured in primary rat hepatocytes by gas chromatography after liquid solid extraction, hydrolysis, isolation by lipophilic anion exchange chromatography and conversion to methyl ester-trimethylsilyl ether derivatives as described previously (Kren et al., *Am. J. Physiol.*, 269, G961–973 (1995)). Identification of intracellular bile acids was made on the basis of gas chromatography retention index relative to a homologus series of n-alkanes (Lawson et al., The Bile Acids, K. D. R. Setchell et al. (eds.), Vol. 4, Plenum Press, New York, 167–267 (1988)). Quantification of bile acids was achieved using gas chromatography, by comparing the peak height response of the individual bile acids with the peak height response obtained from the internal standard, nordeoxycholic acid, which was added to each sample prior to bile acid extraction.

Incubation of cells with ethanol, TGF-$\beta$1, anti-Fas antibody or okadaic acid. Freshly isolated rat hepatocytes were cultured for 3 h as described above and then incubated with William's E medium supplemented with either 0.5% ethanol, 50 KM UDCA, ethanol plus UDCA, or no addition (control) for 2 h and 4 h. HuH-7 cells were incubated with Dulbecco's medium supplemented with either 1 nM TGF-$\beta$1 (R & D Systems, Minneapolis, Minn.), 100 FM UDCA, TGF-β1+UDCA, or no addition (control) for 24 h, 48 h, and 72 h. Hep G2 cells were incubated with Dulbecco's medium supplemented with either 0.5 µg/ml of anti-Fas antibody CH-11 (Upstate Biotechnology, Inc., Lake Placid, N.Y.), 100 µM UDCA, CH-11+UDCA, or no addition for 48 h. Both HuH-7 cells and human osteogenic sarcoma Saos-2 cells were cultured in Dulbecco's medium supplemented with either 50 nM okadaic acid (Boehringer Mannheim Biochemicals, Inc, Indianapolis, Ind.), 100 µM UDCA, okadaic acid+UDCA, or no addition for 48 h. In all the combination groups, cells were pretreated with UDCA alone for 60 min prior to addition of ethanol, TGF-β1, anti-Fas antibody or okadaic acid.

HuH-7 cells were treated with 1 nM TGF-β1, 100 µM of either hyodeoxycholic acid, taurocholic acid, tauroursodeoxycholic acid (Sigma Chemical Co.) or glycoursodeoxycholic acid (Steraloids Inc., Wilton, N.H.), or a combination of TGF-β1 plus the individual bile acids for 72 h. HeLa and Cos-7 cells were incubated with 50 nM okadaic acid, 100 µM of either tauroursodeoxycholic acid or glycoursodeoxycholic acid, or a combination of okadaic acid plus the individual bile acids for 24 h. In the combination groups, cells were pretreated with the bile acid alone for 60 min prior to incuation with TGF-β1 or okadaic acid. In all studies, the medium was gently removed at the indicated times and scored for nonviable cells. The attached cells were fixed for morphologic evaluation of apoptosis.

Morphological evaluation of apoptosis. Morphology was performed as described previously (Oberhammer et al., Proc. Natl. Acad. Sci. USA, 89, 5408–5412 (1992)). Briefly, after fixation (with 4% formaldehyde in PBS, pH 7.4, for 10 min at room temperature), the cells were incubated with Hoechst dye 33258 (Sigma Chemical Co.) at 5 µg/ml in PBS for 5 min, washed with PBS and mounted with PBS:glycerol (3:1, v/v). Fluorescence was visualized with a Zeiss standard fluorescence microscope (Carl Zeiss, Inc., Thornwood, N.Y.). Photographs were taken with Kodak Ektar-1000 film (Eastman Kodak Co.). Stained nuclei were scored by blind analysis and categorized according to the condensation and staining characteristics of chromatin. Normal nuclei were identified as noncondensed chromatin dispersed over the entire nucleus. Apoptotic nuclei were identified by condensed chromatin, contiguous to the nuclear membrane, as well as nuclear fragmentation of condensed chromatin. Three fields per dish of approximately 500 nuclei were counted; mean values are expressed as the percent of apoptotic nuclei.

Annexin V-Biotin assay. The annexin V-biotin apoptosis assay was performed on HuH-7 cells according to the manufacturer's recommendations (R & D Systems). In short, annexin V-biotin was added to HuH-7 cells at $2 \times 10^4$ cells/ml on a 96-well, flat bottom, MICROTEST III tissue culture plate (Becton Dickinson Labware) after incubation with either 100 µM DCA, UDCA, their combination, or no bile acid addition (control) for 6 h. The chromogenic signal generated from the binding of annexin V to exposed phosphatidylserine moieties was read at 450 nm using a microplate reader (Molecular Devices, Co., Menlo Park, Calif.).

Isolation of mitochondria and MPT assays. Low calcium liver mitochondria were isolated from male 200–250 g Sprague-Dawley rats by density gradient centrifugation as previously published (Botla et al., J. Pharmacol. Exp. Ther., 272, 930–938 (1995); Walaitys-Rhode et al., J. Biol. Chem., 267, 370–379 (1992); and Sokol et al., Gastroenterolozy, 99, 1061–1071 (1990)). The mitochondrial fraction was resuspended in 30 ml of wash buffer containing 0.1 M KCl, 5 mM 3-(N-morpholino)-propane sulfonic acid (MOPS), and 1 mM EGTA, at pH 7.4 and centrifuged at 7,000×g for 10 min at 4° C. A final wash was carried out in chelex-100-treated buffer (Bio-Rad Laboratories, Hercules, Calif.) containing no EGTA. The resulting pellet was suspended in 4 ml of chelex-100-treated buffer containing 125 mM sucrose, 5 mM HEPES, 50 mM KCl and 2 mM $KH_2PO_4$. The usual yield of mitochondria was approximately 25 mg of protein per gram of liver tissue. Mitochondrial purity was established as previously described (Botla et al., J. Pharmacol. Exp. Ther., 272, 930–938 (1995)). Protein concentrations were determined using the Bio-Rad protein assay kit as specified by the manufacturer.

MPT was measured spectrophotometrically as described previously (Botla et al., J. Pharmacol. Exp. Ther., 272, 930–938 (1995); Pastorino et al., J. Biol. Chem., 268, 13791–13798 (1993)), during 10 min incubations at 25° C. using mitochondria (1 mg of protein/ml) suspended in 3 ml of a chelex-100-treated buffer containing 0.1 µM NaCl, 10 mM MOPS, pH 7.4. Swelling was monitored at 540 nm in a Beckman DU 64 spectrophotometer. Basal values of mitochondria absorbance were measured for 5 min, and the optical density was monitored another 5 min after addition of 200 µM DCA or 80 µM phenylarsine oxide (PhAsO; Sigma Chemical Co.). For coincubation studies, mitochondria were preincubated with 500 µM UDCA or hyodeoxycholic acid for 5 min at 25° C. prior to the assay. Inhibition of DCA-induced MPT by cyclosporine A (Sigma Chemical Co.) was measured as described previously (Botla et al., J. Pharmacol. Exp. Ther., 272, 930–938 (1995)).

$\Delta\Psi_m$ and ROS measurement. $\Delta\Psi_m$ and ROS production were measured by FACScan (Becton Dickinson) analysis. Freshly isolated rat hepatocytes were cultured for 3 h as described above and then incubated with William's E medium supplemented with either 100 µM DCA, 100 µM UDCA, equal molar amounts of both, or no bile acid (control), for 6 h. Rat hepatocytes were also cultured with either 1% ethanol, 100 µM UDCA, ethanol+UDCA, or no addition (control) for 4 h. HuH-7 cells, Hep G2 cells, and human osteogenic sarcoma Saos-2 cells were incubated with TGF-β1, anti-Fas antibody or okadaic acid, respectively, for 48 h under the same conditions as outlined above. For combination studies, cells were pretreated with UDCA or hyodeoxycholic acid for 60 min prior to addition of DCA, ethanol, TGF-β1, anti-Fas antibody or okadaic acid. Aliquots of $1.0 \times 10^6$ cells were incubated for 15 min at 37° C. with 50 nM 3,3'-dihexyloxacarbocyanine iodide [$DiOC_6$(3)], 2 µM dihydroethidium (HE), or 5 µM 2',7'-dichlorofluorescin diacetate ($H_2DCFDA$; Molecular Probes, Inc. Eugene, Oreg.) and analyzed by cytofluorometry (Cathcart et al., Anal. Biochem., 134, 111–116 (1983); Zamzami et al., J. Exp. Med., 181, 1661–1672 (1995); Carter et al., J. Leukocyte Biol., 55, 253–258 (1994)).

Statistical analysis. Statistical analysis was performed using InStat version 2.1 for the unpaired Student t tests, ANOVA and Bonferroni's multiple comparison tests.

B. Results

UDCA feeding protects from DCA-induced apoptosis in vivo. We have previously shown that dietary manipulation with DCA and UDCA resulted in marked alterations in composition of the bile acid pool (Kren et al., Am. J. Physiol., 269, G961–G973 (1995)). DCA feeding at the 0.4% level led to an approximately 10-fold hepatic enrichment in this bile acid relative to control animals. Similarly, when UDCA was supplemented and fed to the animals, it becane the predominant bile acid in the liver. We investigated whether apoptosis is involved in the process of bile acid-induced injury to the liver. Cryosections of liver tissue from rats fed bile acids were assayed for the characteristic fragmented DNA of apoptosis using digoxigenin-labeling (FIG. 1A). After feeding DCA to rats, TUNEL assays revealed 11% of the liver cells exhibited positive nuclear staining for fragmented DNA, a 40-fold increase from control values (P<0.001). Conversely, only a 2-fold increase was detected in the liver tissue of rats fed UDCA. When the two bile acids were combined in the diet, UDCA completely inhibited cell death by apoptosis associated with the hydrophobic bile acid alone. In fact, the number of apoptotic cells was slightly lower than in control animals (FIG. 1B).

Determination of bile acid concentrations in primary rat hepatocytes and HuH-7 cells. Bile acid levels were measured by gas chromatography in primary rat hepatcytes incubated for 6 h with 50 $\mu$M of either DCA, UDCA, or their combination. Changes in intracellular bile acid composition paralleled those for liver tissue in rats fed a diet supplemented with the same bile acids (Kren et al., *Am. J. Physiol.*, 269 G961–G973 (1995)). Specifically, there was a marked intracellular increase in DCA from 3.0±0.9 nmol to 49.5±9.9 nmol/$10^8$ cells incubated with DCA alone (P<0.001). Similarly, UDCA was detected in low concentration in control hepatocytes (2.3±1.7 nmol/$10^8$ cells) but was the major intracellular bile acid during UDCA treatment (306.0±135.1 nmol, P<0.01). Cholic acid, which normally accounted for more than 70% of the bile acids in primary rat hepatocytes, was slightly higher after DCA treatment (28.8±8.8 nmol vs. 17.3±5.0 nmol/$10^8$ cells) and lower after UDCA incubation (11.9±2.4 nmol). Combining the two bile acids led to a considerable increase in the intracellular concentration of DCA (380.3±32.0 nmol/$10^8$ cells, P<0.001) and no significant change in UDCA (263.8±39.3 nmol) when compared with incubating primary rat hepatocytes with the individual compounds. A concomitant increase occurred in the intracellular concentration of cholic acid (165.1±37.5 nmol/$10^8$ cells, P<0.001).

Bile acid concentrations were also measured by gas chromatography in HuH-7 cells that were incubated with 100 $\mu$M of either DCA, UDCA, or a combination for 6 h. With DCA or UDCA incubation, each became the predominant species and increased from control levels of 2.5±1.0 to 28.8±13.3 nmol (P<0.001) and 1.2±0.6 nmol to 204.7±97.2 nmol/$10^8$ cells (P<0.001), respectively. Cholic acid, however, decreased from 13.5±1.0 nmol to 4.8±0.2 nmol and 2.6±0.2 nmol/$10^8$ cells, respectively (P<0.001). Coincubation with both bile acids led to a pronounced decrease in the intracellular concentration of UDCA (45.5±21.5 nmol, P<0.001) even though the DCA concentration did not change significantly (31.7±15.0 nmol) from DCA alone.

Figure 2A:
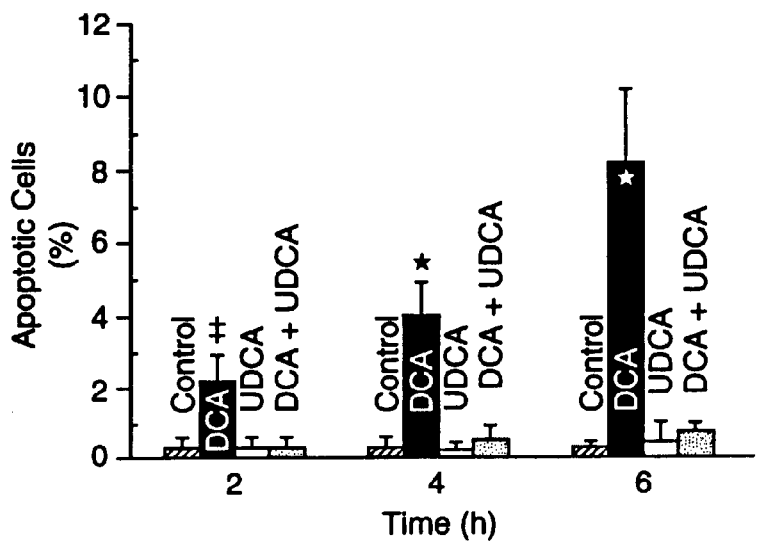
FIG. 2. Bile acid-induced apoptosis in primary rat hepatocytes and HuH-7 cells.
(FIG. 2B) HuH-7 cells were grown with varying doses of DCA for 6 h in Dulbecco's MEM medium supplemented with 10% FBS . The percent apoptosis after incubation with increasing doses of DCA was determined by fluorescence microscopy of Hoechst-stained nuclei. The results are means±S.D. from at least four different experiments. ‡$P<0.05$; *$P<0.001$ from controls.

UDCA inhibits DCA-induced apoptosis in vitro. Cell culture studies confirmed that the apoptotic changes observed in vivo after DCA feeding also occurred in cultured primary rat hepatocytes after incubation with DCA. Apoptosis was assessed by changes in nuclear morphology revealed by Hoechst staining and was characterized by condensation of chromatin and nuclear fragmentation with formation of apoptotic bodies. Significant changes were detected in the number of apoptotic cells when hepatocytes were treated with 50 $\mu$M DCA and a maximum apoptotic response was exhibited at 6 h (FIG. 2A). The percentage of apoptotic cells increased from 8-fold over control after 2 h incubation to greater than 40-fold after 6 hours. Incubation with UDCA alone produced no significant changes in nuclear morphology compared to controls. In addition, UDCA protected against DCA-induced apoptosis and increased cell viability to 88.5±4.9% at 6 h (P<0.001).

Figure 2B:
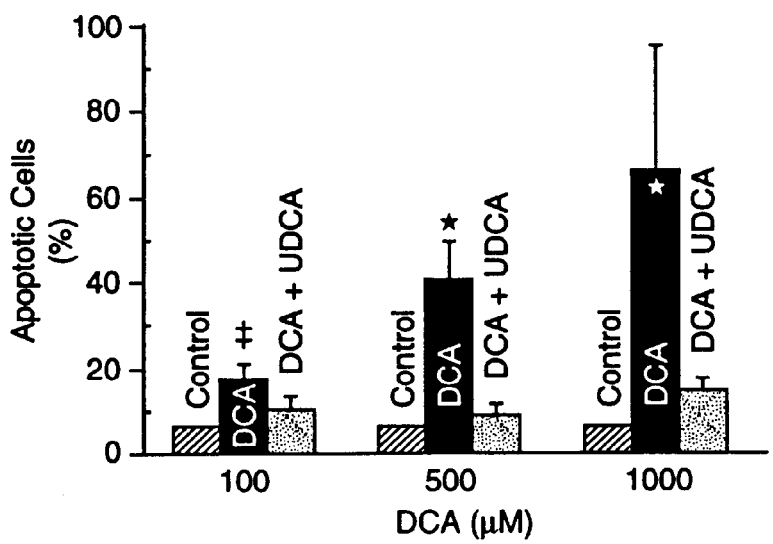

DCA-induced apoptosis in HuH-7 hepatoma cells. HuH-7 cells are a well-differentiated human hepatoma cell line which exhibit characteristic apoptotic changes to TGF-$\beta$1 (Fan et al., *Oncogene*, 12, 1909–1919 (1996)). To establish a dose response of apoptosis with DCA, HuH-7 cells were exposed for 6 h to various concentrations of bile acids. Cells incubated with 50 $\mu$M DCA retained their characteristic nuclear morphology; but incubation with 100 $\mu$M of DCA or greater resulted in apoptotic changes (FIG. 2B). Comparatively, cells treated with the same concentration of UDCA exhibited normal morphology and increased abundance. When no bile acid was added to the incubation medium, approximately 6% of cells exhibited apoptotic nuclei by fluorescence microscopy. With increasing concentrations of DCA, the percent of apoptotic cells increased from 16.8% at 100 $\mu$M to 66.7% at 1000 $\mu$M. Interestingly, no apparent necrosis of HuH-7 cells was observed at these elevated bile acid concentrations, perhaps reflecting the lower intracellular concentrations of bile acids compared to the isolated hepatocytes. No significant difference from control was observed when cells were incubated with similar concentrations of UDCA alone. Furthermore, UDCA significantly inhibited the apoptosis induced by DCA. At 24 h, 20±2.8% of the 100 $\mu$M DCA-treated cells were apoptotic while only 11.5±2.1% of the combination treated cells exhibited apoptosis. In addition, cell viability was increased 44±7.1% by coincubation with UDCA.

DCA induces phosphatidylserine externalization in the cell membrane of HuH-7 cells. Phosphatidylserine is predominantly located in the inner leaflet of the plasma membrane of normal cells. With apoptosis, however, phosphatidylserine is rapidly translocated to the outer leaflet, in part, through a flippase mechanism. In fact, externalization of the fatty acid head groups occurs earlier in apoptosis than detectable nuclear changes. We, therefore, examined the effect of DCA on such an early event at the surface membrane of HuH-7 cells. The annexin V-biotin assays confirmed the results previously obtained by morphological evaluation of apoptosis and indicated that the hydrophobic bile acid DCA induces phosphatidylserine externalization in HuH-7 cell plasma membrane. The optical density at 450 nm wavelength was 0.27±0.06 (P<0.001), 0.08±0.02 and 0.09±0.04 for DCA, UDCA, and DCA+UDCA treated cells relative to controls.

Figure 3:
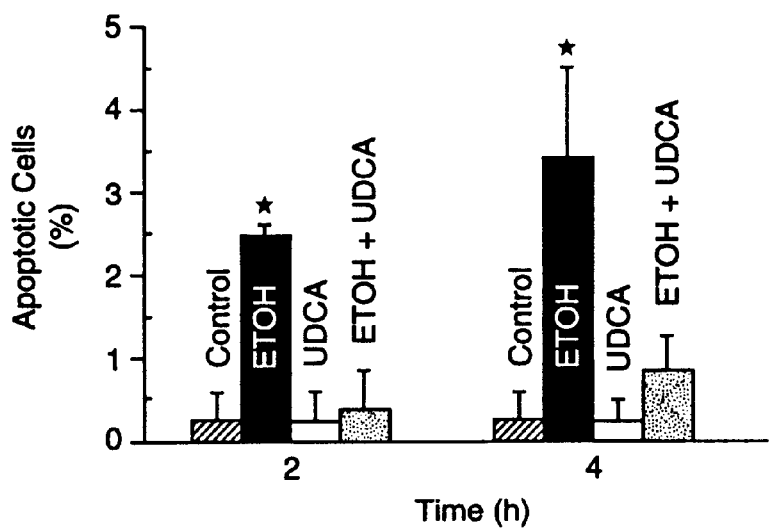
FIG. 3. Alcohol-induced apoptosis in primary rat hepatocytes. Cells were grown with either 0.5% ethanol (ETOH), 50 μM UDCA, a combination of the two, or no bile acid (control) in William's E medium supplemented with 10% FBS . Cells were fixed and stained with Hoechst 33258 to detect nuclear fragmentation and condensed chromatin. The percent apoptosis after treatment with either ETOH, UDCA, the combination, or no addition was determined at 2 h and 4 h. The results are representative of at least four different experiments. *$P<0.001$ from controls.

UDCA inhibits alcohol-, TGF-$\beta$1-, anti-Fas antibody- and okadaic acid-induced apoptosis. Primary rat hepatocytes incubated with 0.5% ethanol exhibited a 10-fold increase in apoptosis over control values after 2 h (P<0.001) and apoptosis continued to increase by 4 h (FIG. 3). Coincubation with UDCA protected against ethanol-induced apoptosis, reducing the apoptotic response and increasing cell viability (79.5±7.9%) to control values. In contrast, no inhibitory effect was detected when cells were coincubated with DCA.

Figures 4A, 4B:
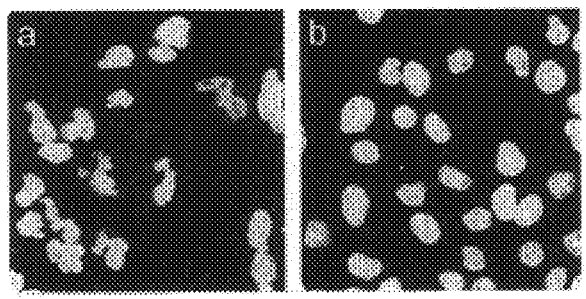
(FIG. 4A) Apoptotic changes determined with Hoechst staining in cells treated for 72 h with TGF-β1(a) and TGF-β1+UDCA (b). Percent apoptosis (lower panel) in cells treated with either 1 nM TGF-β1 , 100 μM UDCA, the combination, or no addition (control) after 24 h, 48 h, and 72 h of incubation. Apoptotic cells were identified by morphological changes associated with condensed chromatin, fragmentation and apoptotic bodies.
(FIG. 4B) Hep G2 cells were incubated with 0.5 μg/ml of either anti-Fas antibody (CH-11), UDCA, a combination of CH-11+UDCA, or no addition (control) in Dulbecco's MEM medium supplemented with 10% FBS. Cells were then fixed and characterized for apoptotic changes. The percent apoptosis in cells treated with CH-11, UDCA, or the combination was determined after 48 h of incubation. The results are means±S.D. from a minimum of four different experiments. $^§P<0.05$; *$P<0.001$ from controls; ‡$P<0.05$ from TGF-β1 alone. No signifigant changes were observed between control, UDCA, and anti-Fas antibody plus UDCA.

We investigated the ability of UDCA to inhibit apoptosis induced by other nonmembrane damaging agents. In this regard, HuH-7 cells displayed a maximum apoptotic response to TGF-$\beta$1 at 72 h in agreement with that reported previously (Fan et al., *Oncogene*, 12, 1909–1919 (1996)). With prolonged exposure to TGF-$\beta$1, cell nuclei progressed from two to three blebs with some chromatin condensation after 24 h, to increased chromatin condensation and three to four nuclear blebs after 48 h and even greater nuclear fragmentation by 72 h (FIG. 4A,*a*). Addition of UDCA to the incubation media significantly decreased TGF-$\beta$1 apoptosis by approximately 49%, 44%, and 45% at 24 h, 48 h, and 72 h, respectively (FIG. 4A, lower panel). Similar changes in cell viability determined by trypan blue exclusion were also observed with UDCA coincubation for 48 h and 72 h (P<0.001). Moreover, addition of the tauro- and glyco-conjugated derivatives of ursodeoxycholic acid to the culture medium also inhibited TGF-β1-induced apoptosis in HuH-7 cells at 72 h by 45.8±7.9 and 37.5±5.1%, respectively (P<0.001). In contrast, neither hyodeoxycholic acid nor taurocholic acid showed inhibition of apoptosis (data not shown).

We then determined whether UDCA could inhibit apoptosis induced by the Fas ligand (Nagata et al., *Science*, 267, 1449–1456 (1995)). To do so, we incubated Hep G2 cells with 0.5 µg/ml of the CH-11 monoclonal anti-Fas antibody and examined the cells at 48 h (FIG. 4B). Approximately 10% of the cells exhibited apoptotic changes compared to a control value of 1.2% (P<0.001). Interestingly, UDCA alone decreased the incidence of apoptosis slightly to 0.7%, while the concurrent treatment of the Hep G2 cells with UDCA and anti-Fas antibody resulted in no significant increase in apoptosis over control values.

Figures 5A, 5B:
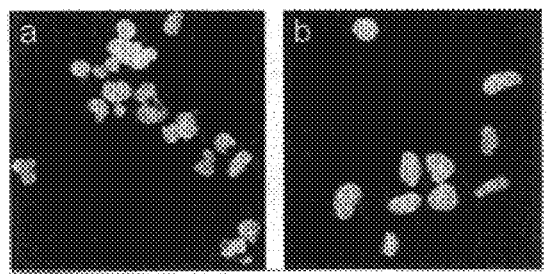
FIG. 5. Inhibition of okadaic acid-induced apoptosis in HuH-7 and Saos-2 cells by UDCA. Cells were incubated with either 50 nM okadaic acid (OA), UDCA, a combination of okadaic acid and UDCA, or no addition (control) and evaluated for apoptosis. Fluorescence microscopy of Hoechst staining 48 h after incubation of HuH-7 cells (FIG. 5A, top) with okadaic acid (a) and with okadaic acid+UDCA (b). Incubation with okadaic acid was associated with a significant increase in apoptosis in both HuH-7 and Saos-2 cells (FIGS. 5A and 5B, lower panels; $P<0.001$). A significant decrease ($P<0.001$) in apoptosis was observed when the cells were treated with okadaic acid+UDCA, but the reduced level of apoptosis was still greater than that observed in the untreated or UDCA-treated cells ($P<0.05$). The results are means±S.D. from three to five different experiments. *$P<0.001$ from all others.

We have shown that okadaic acid is a strong apoptotic stimulus in both HuH-7 and the human osteogenic sarcoma Saos-2 cells (G. Fan et al., *Oncogene*, 12:1909–1919 (1996)). We examined the ability of UDCA to inhibit apoptosis induced by 50 nM okadaic acid to determine whether the effect is observed in nonhepatocyte cells. Incubation with okadaic acid induced apoptosis in 30% to 40% of both cell types (FIGS. 5A and 5B). Although incubation with UDCA and 50 nM okadaic acid did not completely inhibit the apoptotic response, it was reduced by>80% (P<0.001). The ability of UDCA to protect against okadaic acid-induced apoptosis was also assessed in cultured HeLa and Cos-7 cells. UDCA reduced the percent apoptosis from 50.0±14.9 to 20.5±7.1% and 21.4±2.9 to 7.3±2.4% in the HeLa and Cos-7 cells, respectively (P<0.001). Similar protection against the okadaic acid-induced apoptosis in these cells was observed with both glyco- and tauro-conjugated UDCA (data not shown).

UDCA inhibits the MPT induced by DCA. The disruption of mitochondrial function marks the commitment to the apoptotic death process. Thus, mitochondria were isolated from rat liver to determine whether DCA induces MPT. The isolated mitochondrial pellet was highly enriched in mitochondria with minimal contamination by lysosomes or microsomes, as assessed by marker enzyme analysis (data not shown). High amplitude mitochondrial swelling was detected with concentrations as low as 50 µM DCA. Furthermore, pretreatment of the mitochondria with 500 µM UDCA inhibited the 200 µM DCA-induced MPT by 43.1±1.6% (P<0.001). Similarly, cyclosporine A, an inhibitor of the megapore channel, reduced the 200 µM DCA-induced mitochondrial swelling by 45.8±5.4% (P<0.004). UDCA alone produced no significant difference from control values. The specificity of inhibition by UDCA was tested using the hydrophilic bile salt hyodeoxycholic acid. No significant mitochondrial swelling was induced by hyodeoxycholic acid nor did it have a protective effect on the DCA-induced MPT. The isolated mitochondria were then incubated with PhAsO, a potent inducer of MPT, alone or in combination with UDCA. When mitochondria were treated with 500 µM UDCA and then exposed to 80 µM PhAsO, MPT was reduced by 49.6±9.8% (P<0.001). These data suggested that UDCA can function as a general inhibitor of MPT and its role in modulating the apoptotic threshold may be mediated by its protective effect on mitochondrial membrane perturbation.

Interestingly, ethanol did not induce mitochondria swelling nor did the other nonmembrane inducers of apoptosis even when high concentrations of these agents were added to isolated mitochondria.

Figure 6A:
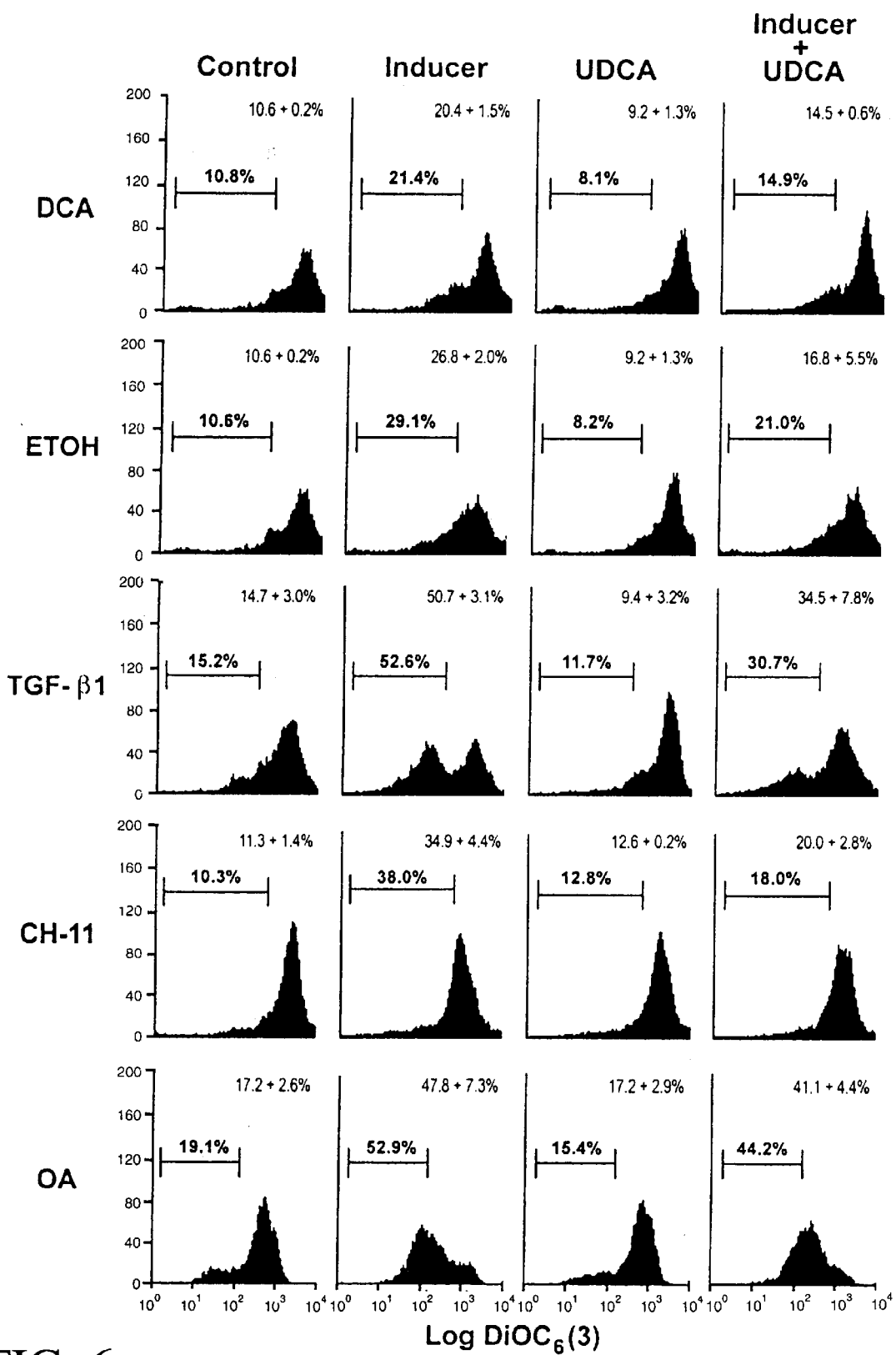
FIG. 6. Reduction of mitochondrial transmembrane potential (abbreviated $\Delta\Psi_m$) and increased production of ROS during apoptosis. Coadministration of UDCA with each of the apoptosis-inducing agents was associated with a significant inhibition of apoptotic changes in all cell types. Hepatocytes were treated with 100 µM DCA and 1% ETOH for 6 h and 4 h, respectively; HuH-7 cells with 1 nM TGF-β1 for 48 h; Hep G2 cells with 0.5 µg/ml anti-Fas antiboby (CH-11) for 48 h; and Saos-2 cells with 50 nM okadaic acid (OA) for 48 h. In all the combination groups, cells were pretreated with 100 µM UDCA alone for 60 min prior to addition of the inducer. Aliquots of $1.0\times10^6$ cells were incubated for 15 min at 37° C. with 50 nM 3,3'-dihexyloxacarbocyanine iodide [DiOC$_6$(3)], or 2 µM dihydroethidium (HE) and analyzed by cytofluorometry. The percentages of representative plots reflect the reduction in $\Delta\Psi_m$[DiOC$_6$(3)] (FIG. 6A) and the increased production of ROS (HE→ethidium) (FIG. 6B) during apoptosis, and the respective inhibition by UDCA. The mean±S.D. of four to five different experiments is indicated at the upper right of each plot.
Figure 6B:
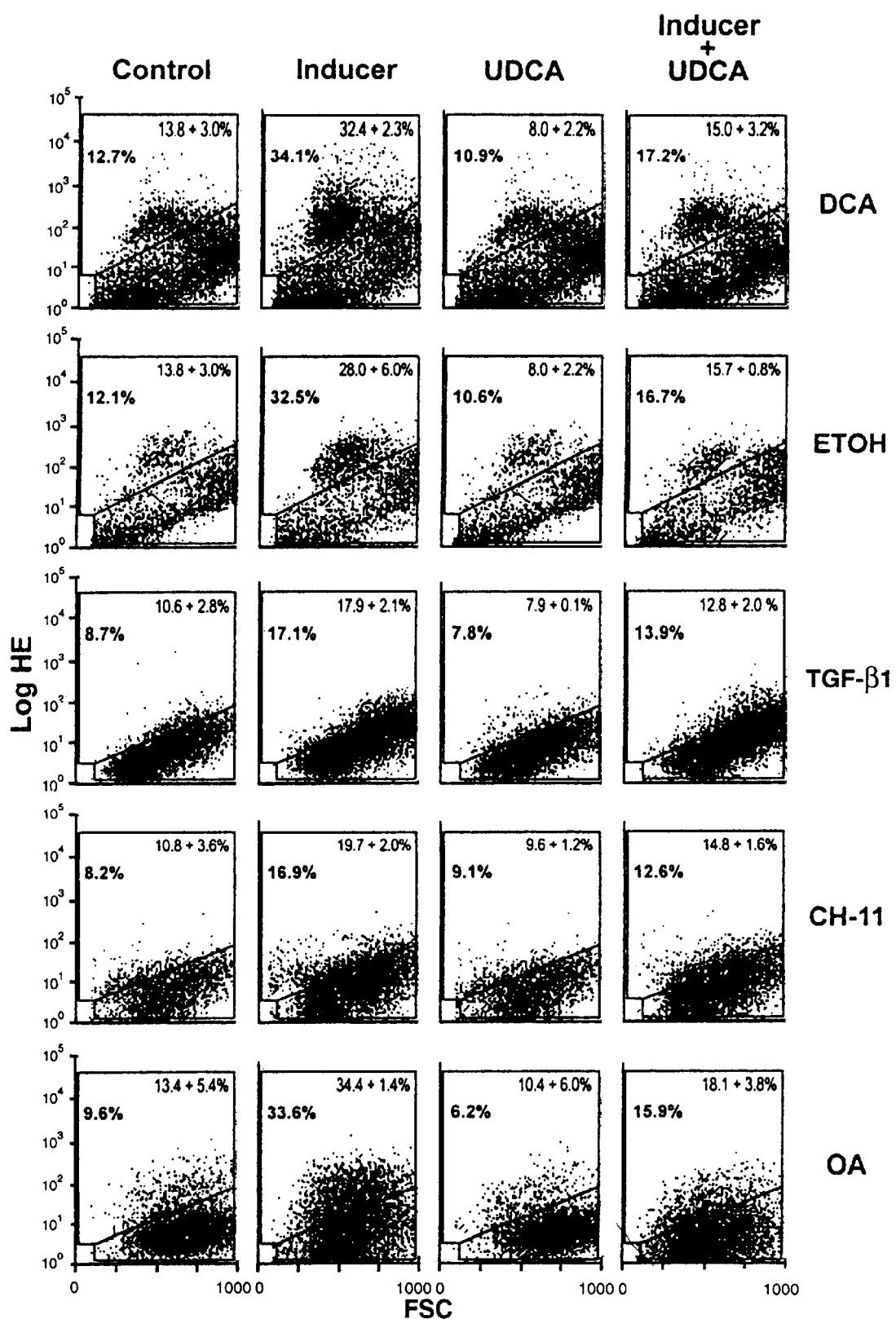

UDCA inhibits disruption of $\Delta\Psi_m$ and production of ROS. The $\Delta\Psi_m$ was measured in the different cell types using the fluorochrome $DiOC_6(3)$ and FACS analysis (Zamzami et al., *J. Exp. Med.*, 181, 1661–1672 (1995)). $\Delta\Psi_m$ was significantly decreased after induction of apoptosis by TGF-β1>okadaic acid>anti-Fas antibody>ethanol>DCA (FIG. 6A). Under the same conditions, FACS analysis revealed the increased production of the ROS superoxide anion as measured by dihydroethidium oxidation to ethidium (Carter et al., *J. Leukocyte Biol.*, 55, 253–258 (1994)). The change was particularly marked for DCA-, alcohol-, and okadaic acid-induced apoptosis but, interestingly, was less pronounced during TGF-β1- and anti-Fas antibody-induced apoptosis (FIG. 6B). Production of other ROS, including hydrogen peroxide and hydroxyl radical was measured using FACS analysis and the fluorochrome $H_2DCFDA$ (Cathcart et al., *Anal. Biochem.*, 134, 111–116 (1983)). These reactive oxygen compounds were also significantly increased during apoptosis when compared to the ROS observed in untreated or UDCA-treated cells (Table 1, below). Both $\Delta\Psi_m$ disruption and ROS production were partially inhibited by coincubation with UDCA, but not with hyodeoxycholic acid. In fact, coadministration of UDCA was associated with a 21–63% inhibition of $\Delta\Psi_m$ disruption (P<0.05) and a 55–93% decrease in superoxide anion production (P<0.05). Increase in other ROS was also inhibited by UDCA from 39–65% (P<0.05). Interestingly, UDCA alone increased $\Delta\Psi_m$ and reduced ROS production compared to control values in all cell types with the exception of Hep G2 cells. Finally, the inhibition of mitochondrial dysfunction by coincubation with UDCA was, in general, quite similar to its ability to inhibit apoptosis by the different agents (Table 2, below).

Table 1. FACS Analysis of Peroxides Production

TABLE 1

| FACS Analysis of Peroxides Production | | | |
|---|---|---|---|
| AGENT | Peroxides Production (%) | | |
| (cell type) | Inducer | Inducer + UDCA | % Inhibition |
| DCA (Hepatocytes) | 12.8 ± 0.9 | 4.4 ± 1.5* | 65.8 ± 12.4 |
| ETOH (Hepatocytes) | 17.9 ± 5.4 | 10.7 ± 3.6§ | 39.5 ± 12.6 |
| TGF-β1 (HuH-7) | 11.0 ± 2.9 | 5.8 ± 2.5§ | 47.3 ± 16.0 |
| CH-11 (Hep G2) | 13.4 ± 1.7 | 6.2 ± 1.3† | 52.2 ± 14.9 |
| OA (Saos-2) | 15.0 ± 1.1 | 5.4 ± 1.5* | 64.6 ± 7.5 |

Rat primary hepatocytes were incubated with 100 µM DCA and 1% ETOH for 6 h and 4 h, respectively; HuH-7 cells with 1 nM TGF-β1 for 48 h; Hep G2 cells with 0.5 µg/ml anti-Fas antibody (CHR-11) for 48 h, and Saos-2 cells with 50 nM okadaic acid (OA) for 48 h. In each combination group, cells were pretreated with 100 µM UDCA alone for 60 min prior to addition of the inducer. Aliquots of $1.0\times10^6$ cells were incubated for 15 min at 37° C. with 5 µM 2',7'-dichlorofluorescin diacetate ($H_2DCFDA$) and analyzed by cytofluorometry. The data reflect the increased production of peroxides during apoptosis, and the respective inhibition by UDCA. The results are representative of three to five different experiments. §P<0.05; †p<0.01; *P<0.001 from inducer alone.

TABLE 2

Inhibition of Apoptosis and Mitochondrial Perturbation by UDCA

| AGENT | Inhibition (%) | | | |
|---|---|---|---|---|
| (cell type) | Apoptosis | $\Psi m$ | Superoxide Anion | Peroxides |
| DCA (Hepatocytes) | 90.9 ± 4.6 | 60.2 ± 6.1* | 93.5 ± 17.2 | 65.8 ± 12.4* |
| ETOH (Hepatocytes) | 75.9 ± 13.8 | 61.7 ± 33.9 | 86.6 ± 5.6 | 39.5 ± 12.6 |
| TGF-β1 (HuH-7) | 44.2 ± 11.2 | 45.0 ± 21.7 | 69.9 ± 15.6 | 47.3 ± 16.0 |
| CH-11 (Hep G2) | 83.2 ± 7.0 | 63.1 ± 11.9 | 55.1 ± 10.8* | 52.2 ± 14.9* |
| OA (Saos-2) | 81.8 ± 2.3 | 21.9 ± 10.7* | 77.6 ± 18.1 | 64.6 ± 7.5 |

*Statistically significant decrease from % inhibition of apoptosis ($P < 0.001$ for OA; $P < 0.05$ for all others).

Data calculated from FIGS. 2–6 and Table 1.

Example II

Ursodeoxycholic Acid Inhibits Deoxycholic Acid-Induced Apoptosis by Modulating Mitochondrial Transmembrane Potential and Reactive Oxygen Species Production A. Materials and Methods Animals and Diets. Male 160–175 g Sprague-Dawley rats (Sprague-Dawley, Indianapolis, Ind.), were maintained on a 12 h light-dark cycle and fed standard laboratory chow ad libitum for 3 days. The animals were then transferred to metabolic cages and fed diets of standard laboratory chow supplemented with either no bile acid or 0.4% (wt/wt) DCA, 0.4% UDCA, or a combination of DCA+UDCA (Bio-Serv, Frenchtown, N.J.). On day 10, the animals were sacrificed by exsanguination under ether anesthesia between 9 a.m. and 11 a.m. The livers were removed, rinsed in normal saline, and flash-frozen in liquid nitrogen until western blot analyses of apoptosis-related proteins were performed. All animals received humane care in compliance with the Guide for the Care and Use of Laboratory Animals, prepared by the National Academy of Sciences (NIH Publication No. 86-23, revised 1985).

Mitochondrial Isolation. Low calcium liver mitochondria were isolated from adult male 200–250 g Sprague-Dawley rats as previously published (Botla et al., *J. Pharmacol. Exp. Ther.*, 272, 930–938 (1995); Walajtys-Rhode et al., *J. Biol. Chem.*, 267, 370–379 (1992)). In short, animals were sacrificed by exsanguination under ether anesthesia and the livers removed and rinsed in normal saline. Approximately 10 g of minced liver was homogenized in an ice-cold solution of 70 mM sucrose, 220 mM mannitol, 1 mM EGTA and 10 mM HEPES, pH 7.4 as a 10% (wt/vol) homogenate. After 2 low speed centrifugations, a crude mitochondrial pellet was purified by sucrose-percoll gradient centrifugation (Sokol et al., *Gastroenterology*, 99, 1061–1071 (1990)). The pellet was resuspended in 2 ml of homogenate buffer, and 1 ml of the resuspended pellet was carefully layered onto a 35 ml self-generating gradient containing 0.25 μM sucrose, 1 mM EGTA and percoll (75:25, vol/vol). The mitochondria were purified by centrifugation at 43,000×g for 30 min at 4° C. using a Beckman Ti60 rotor and a Beckman ultracentrifuge model L8-55 (Beckman Instruments, Inc., Schaumburg, Ill.). The clear supernatant solution was removed and the lower turbid layer was resuspended in 30 ml of wash buffer containing 0.1 μM KCl, 5 mM $^3$-(N-morpholino)-propane sulfonic acid (MOPS), and 1 mM EGTA, at pH 7.4 and centrifuged at 7,000×g for 10 min at 4° C. A final wash was carried out in chelex-100-treated buffer (Bio-Rad Laboratories, Hercules, Calif.) without EGTA. The pellet was suspended in 4 ml of chelex- 100-treated resuspension buffer containing 125 mM sucrose, 5 mM HEPES, 50 mM KCl and 2 mM $KH_2PO_4$. The usual yield of mitochondria was approximately 25 mg of protein per gram of liver tissue.

Marker Enzyme and Protein Analysis. Mitochondrial fractions were analyzed for mitochondrial malate dehydrogenase (Dupourque et al., *Methods Enzymol.*, 13, 116–122 (1969)), lysosomal N-acetyl-βB-glucosaminidase (LaRusso et al., *J. Clin. Invest.*, 64, 948–954 (1979)) and microsomal esterase (Beaufay et al., *J. Cell Biol.*, 61, 188–200 (1974)) enzymes as described previously. Protein concentrations were determined using the Bio-Rad protein assay (Bio-Rad Laboratories) as recommended by the manufacturer. Mitochondrial preparations were also examined for purity by phase contrast microscopy.

Spectrophotometric and Fluorimetric Assays of MPT. The MPT was assessed using a spectrophotometric assay measuring high amplitude rapid changes in mitochondrial volume, and a fluorimetric assay quantitating the release of calcein from calcein-loaded mitochondria. The MPT was measured spectrophotometrically as previously described (Pastorino, *J. Biol. Chem.*, 268, 13791–13798 (1993); Botla et al., *J. Pharmacol. Exp. Ther.*, 272, 930–938 (1995)). Briefly, mitochondria (3 mg protein) were incubated in 3 ml of chelex-100-treated respiration buffer (0.1 μM NaCl, 10 mM MOPS, pH 7.4) for 10 min at 25° C. and monitored at 540 nm in a Beckman DU 64 spectrophotometer. Basal values of mitochondrial absorbance were measured for 5 min, and the optical density was monitored for an additional 5 min after addition of increasing concentrations of DCA (50–200 μM) or 80 μM phenylarsine oxide (PhAsO; Sigma Chemical Co., St. Louis, Mo.). For the coincubation studies, mitochondria were preincubated with UDCA (100–500 μM), or 500 μM hyodeoxycholic acid (HDCA; Sigma Chemical Co.) for 5 min at 25° C. prior to initiation of the assay. The inhibition of MPT by cyclosporine A (Sigma Chemical Co.) was determined as described previously (Botla et al., *J. Pharmacol. Exp. Ther.*, 272, 930–938 (1995)).

The fluorimetric assay was performed after loading the mitochondria with 10 μM calcein-acetoxymethyl ester (AM) (Molecular Probes Inc., Eugene, OR) for 30 min at 37° C. in chelex-100 treated resuspension buffer before purification by sucrose-percoll gradient centrifugation (Botla et al., *J. Pharmacol. Exp. Ther.*, 272, 930–938 (1995)). The assays were performed using calcein-loaded isolated mitochondria (1 mg protein/ml) in chelex- 100-treated respiration buffer at 37° C. For the coincubation assays, the samples were preincubated for 10 min with 500 μUDCA prior to addition of 200 μM DCA. The fluorescence of calcein was monitored by excitation and emission wavelengths of 490 nm and 515 nm, respectively, using a Perkin-Elmer luminescence spectrometer model LS-5B (Perkin-Elmer Ltd., Buckinghamshire, England).

Measurement of $\Delta\Psi_m$ and ROS Production by FACS Analysis. $\Delta\Psi_m$ and ROS production were measured by FACScan (Becton Dickinson, San Jose, Calif.) analysis. Freshly isolated rat mitochondria were resuspended in respiration buffer (50–100 μg/ml) and then incubated for 15 min at 37° C. with 50 nM 3,3'-dihexyloxacarbocyanine iodide [DiOC$_6$(3)], 2 µM dihydroethidium (HE), or 5 µM 2',7'-dichlorofluorescin diacetate (H$_2$DCFDA; Molecular Probes Inc.) (Cathcart et al., *Anal. Biochem.*, 134, 111–116 (1983); Carter et al., *J. Leukoycte Biol*, 55, 253–258 (1994); Zamzami et al., *J. Exp. Med.*, 181, 1661–1672 (1995)). Mitochondria were then treated with DCA (100 µM) or PhAsO (80 µM) for 5 min and analyzed by cytofluorometry. For the coincubation studies, mitochondria were preincubated with UDCA (500 µM) or HDCA (500 M) prior to the addition of either DCA or PhAsO.

Western Blot Analysis. Cytoplasmic proteins were isolated from rat liver tissue as described previously (Trembley et al., *Cell Growth & Differ.*, 7, 903–916 (1996)). Briefly, frozen liver tissue from bile acid fed rats was ground to a powder in liquid nitrogen using a mortar and pestle followed by Dounce homogenization in hypotonic buffer containing 10 mM Tris, pH 7.6, 5 mM MgCl$_2$, 1.5 mM KAc, 2 mM DTT, supplemented with the COMPLETE protease inhibitor cocktail (Boehringer Mannheim Biochemicals, Inc., Indianapolis, Ind.) at 4° C. Total liver lysate obtained by Dounce homogenization was centrifuged at 4° C. for 10 min at 500×g and the resulting supernatant was centrifuged a second time. Mitochondria were isolated from frozen liver tissue as described above using buffers supplemented with the protease inhibitor cocktail. Cytoplasmic and mitochondrial protein concentrations were determined using the Bio-Rad protein assay (Bio-Rad Laboratories). Proteins were separated using 15% (30:0.2) SDS-PAGE and electrophoretically transferred to nitrocellulose membrane. The membranes were processed for protein detection using the ECL system from Amersham Life Science, Inc. (Arlington Heights, Ill.) as described previously (Trembley et al., *Cell Growth & Differ.*, 7, 903–916 (1996)). The primary antibodies used were: Bax-polyclonal sc-6236; p53-monoclonal sc-99; c-Myc-polyclonal sc-764 (Santa Cruz Biotechnology, Inc., Santa Cruz, Calif.); Bad-monoclonal B36420; Bcl-2-monoclonal B46620; Bcl-X$_L$-polyclonal B22630 (Transduction Laboratories, Lexington, Ky.); and Rb-monoclonal XZ161 (Dr. Ed Harlow, Boston, Mass.).

Densitometry. Video densitometry was accomplished using a Macintosh II (Apple Computer, Cupertino, Calif.) coupled to a Data Translation DT2255 video digitizer (Data Translation, Marlboro, Mass.) and a JVC GX-N8 video camera (JVC Corporation of America, Elmwood Park, N.J.) as described previously (Kren et al., *J. Cell Biol.*, 123, 707–718 (1993)). Quantitation of the autoradiograms was performed using the NIH Image 1.4 densitometric analysis program.

Statistical Analysis. Statistical analysis was performed using InStat version 2.1 for the ANOVA and Bonferroni's multiple comparison tests. Unless otherwise indicated, results are expressed as mean values±standard deviation (S.D.).

B. Results

Figure 7A:
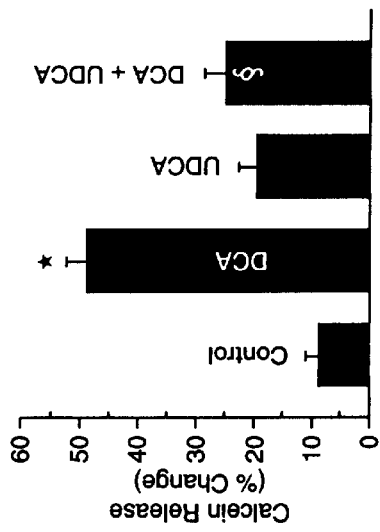
(FIG. 7A) Percent change in mitochondrial swelling was measured by monitoring the optical density at 540 nm. At time zero, 200 µM DCA was added and swelling was monitored for an additional 5 min. In the coincubation experiments, mitochondria were preincubated with 500 µM UDCA for 5 min.
Figure 7B:
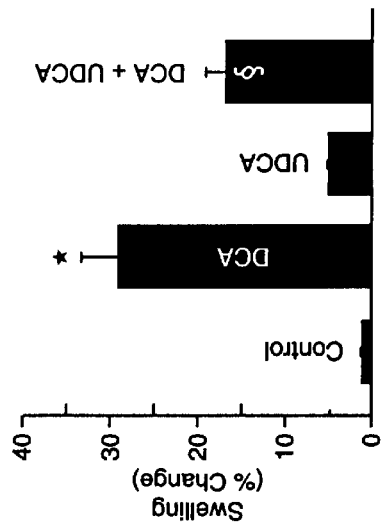
(FIG. 7B) Percent change in calcein release from calcein-loaded mitochondria was measured by monitoring the fluorescence using excitation and emission wavelengths of 490 and 515 nm, respectively. At time zero, 200 µM DCA was added and fluorescence was monitored for an additional 20 min. In the coincubation experiments, mitochondria were pretreated with 500 µM UDCA for 10 min. Values are mean±standard deviations (S.D.) of at least five different experiments. *$p<0.001$ from controls; §$p<5p<0.001$ from DCA.

UDCA Inhibits DCA-induced MPT Phase contrast microscopy of the isolated mitochondria indicated that they were intact, free of contamination, and exhibited minimal clumping. In addition, the purity of the isolated mitochondrial fraction was assessed by marker enzyme studies. As shown in Table 3, below, the purified mitochondrial pellet was highly enriched in mitochondrial malate dehydrogenase activity with minimal contamination by lysosomal N-acetyl-β-glucosaminidase or microsomal esterase activity. Having established the authenticity of the mitochondrial fraction, the MPT was measured using spectrophotometric and fluorimetric methods (FIG. 7A and 7B). It has been previously reported that incubation with glycochenodeoxycholic acid resulted in hepatocyte toxicity (Spivey et al., *Clin. Invest.*, 92, 17–24 (1993)) and induced MPT in isolated rat liver mitochondria (Botla et al., *J. Pharmacol. Exp. Ther.*, 272, 930–938 (1995); Sokol et al., *Hepatology*, 17, 869–881 (1993)). In this study, incubation with DCA also induced significant changes in the MPT of isolated hepatic mitochondria (FIG. 7A). Mitochondrial swelling increased 25-fold over control after a 5 min incubation with DCA ($p<0.001$). In contrast, incubation with UDCA alone produced no significant changes in permeability relative to control values. Moreover, coincubation with UDCA protected against DCA-induced mitochondrial swelling by>40% $p<0.001$). Membrane permeability was also assessed using calcein-loaded mitochondria. In fact, incubation with DCA resulted in significant unquenching of calcein fluorescence, indicative of increased mitochondrial leakage (FIG. 7B). Coincubation with UDCA inhibited DCA-induced calcein release from mitochondria by almost 50% ($p<0.001$), in agreement with the observed inhibition of mitochondrial swelling.

TABLE 3

Enzymatic activities in fractionated mitochondria

| Enzymes | Specific Activity[a] | | Relative Enrichment[b] |
|---|---|---|---|
| | Homogenate | Pellet | |
| Malate dehydrogenase | 1.14 ± 0.25 | 4.05 ± 0.25 | 3.64 ± 0.44 |
| N-acetyl-β-glucosaminidase | 1.25 ± 0.12 | 0.68 ± 0.17 | 0.56 ± 0.13 |
| Microsomal esterase | 0.50 ± 0.04 | 0.07 ± 0.01 | 0.14 ± 0.06 |

Mitochondria were isolated from rat liver by sucrose-percoll gradient centrifugation. Data are mean ± standard deviation (S.D.) from at least three different experiments.
[a]Specific activity represents units of enzyme activity/mg protein for malate dehydrogenase and microsomal esterase. Specific activity for N-acetyl-β-glucosaminidase represents milliunits of enzymatic activity/mg protein.
[b]Relative enrichment represents the specific activity for the respective enzyme in the pellet relative to the specific activity in the homogenate.

Figure 8A:
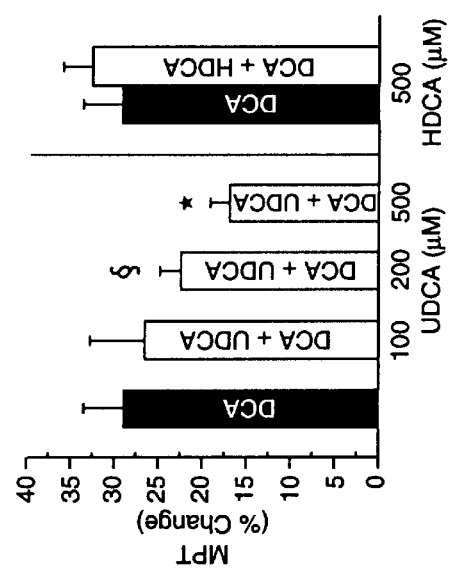
(FIG. 8A) Dose-response to DCA. At time zero, 50–200 µM DCA or 80 µM PhAsO was added and mitochondrial swelling was monitored for an additional 5 min. In the coincubation experiments, mitochondria were preincubated with 500 µM UDCA for 5 min.
Figure 8B:
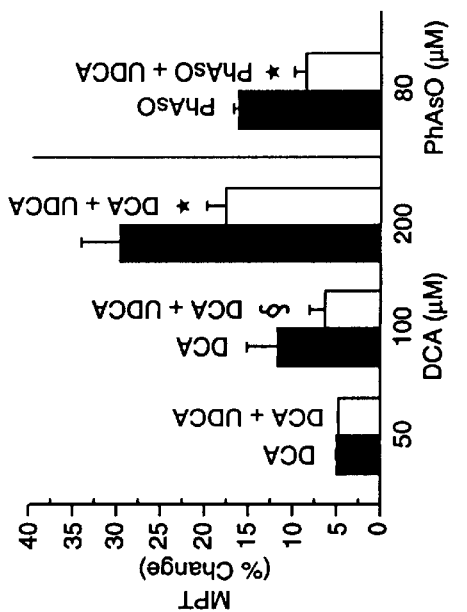
(FIG. 8B) Dose-response to UDCA. At time zero, 200 µM DCA was added and mitochondrial swelling was monitored for an additional 5 min. In the coincubation experiments, mitochondria were pretreated with 100–500 µM UDCA or 500 µM HDCA for 5 min. Values are mean+standard deviations (S.D.) of at least five different experiments. §$p<0.05$ from DCA; *$p<0.001$ from DCA or PhAsO.
Figure 13A:
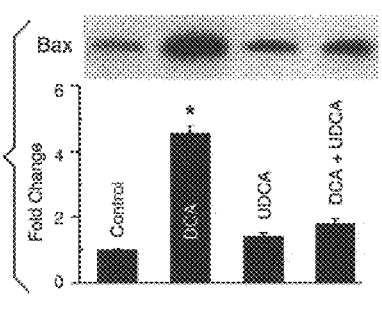
FIG. 13. Western blot analysis of apoptosis-associated proteins in mitochondria isolated from livers of bile acid fed rats. Mitochondrial proteins (150 µg/lane) from control, DCA, UDCA, and DCA+UDCA fed rats were isolated from whole liver. Following SDS-PAGE and transfer, the nitrocellulose membranes were incubated with antibodies to either Bax, Bad, Bcl-2 or Bcl-$X_L$ and the proteins were detected using ECL chemiluminescence. Representative western blots of mitochondrial proteins are shown at top and the accompanying histograms depict the mean changes±S.E.M. in protein levels relative to control. The proteins are indicated on the left and the values shown are from four different animals from each group. *p<0.001 from control; $^\S$p<0.05 from control.
Figure 13C:
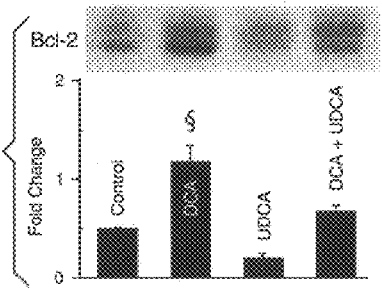
Figure 13B:
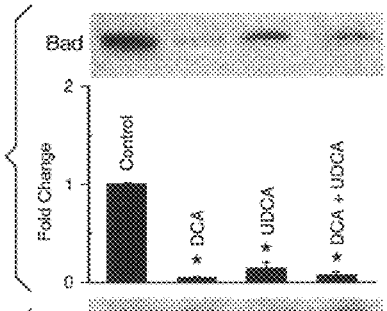
Figure 13D:
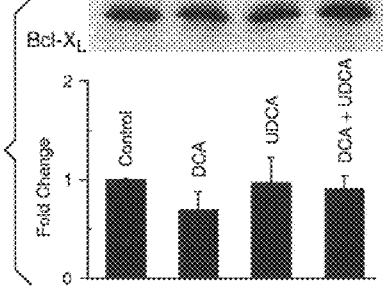

The dose-response effect of DCA on MPT was examined and is shown in FIG. 8A. Incubation with DCA resulted in high amplitude mitochondrial swelling that was rapid and dose-dependent. The observed MPT increased from 4-fold over control after incubation with 50 µM to greater than 25-fold after incubation with 200 µM DCA ($p<0.001$). Significant inhibition of the DCA-induced MPT by 500 µM UDCA occurred in both the 100 ($p<0.05$) and 200 µM DCA ($p<0.001$) treatment groups. Additionally, UDCA inhibited the DCA-induced MPT in a concentration-dependent fashion (FIG. 8B). When mitochondria suspended in respiration buffer were preincubated with increasing concentrations of UDCA for 5 min prior to the addition of 200 µM DCA, swelling decreased from 26.8±6.3% with 100 µM UDCA to 16.9±2.3% with 500 µM UDCA ($p<0.001$). The addition of UDCA after incubation with DCA did not result in significant reversal of MPT (data not shown). We then determined whether the inhibition of the DCA-induced MPT by UDCA was bile acid-specific or simply a property of hydrophilicity. To address this issue, isolated mitochondria were incubated with a similarly hydrophilic bile acid HDCA. Interestingly, pretreatment of the isolated hepatic mitochondria with 500 µM HDCA did not decrease DCA-induced mitochondrial swelling (FIG. 8B) or prevent calcein release.

The significant mitochondrial swelling observed after incubation with DCA suggested that the observed MPT resulted from perturbation of the cyclosporine A/trifluoperazine-sensitive inner membrane large conductance channels (megapores), rather than nonspecific membrane disruption (Pastorino et al., *J. Biol. Chem.*, 268, 13791–13798 (1993); Bernardi, *J. Biol. Chem.*, 267 8834–8839 (1992)). In fact, earlier studies showed that pretreatment of mitochondria with cyclosporine A and/or trifluoperazine inhibited swelling induced by glycine conjugated chenodeoxycholic acid (Botla et al., *J. Pharmacol. Exp. Ther.*, 272, 930–938 (1995)). These observations suggested that UDCA was interacting directly with the mitochondrial membrane and that it might be a general inhibitor of this form of MPT. To test this premise, we incubated isolated mitochondria with either PhAsO, a known inducer of the megapore opening form of MPT (Pastorino et al., *J. Biol. Chem.*, 268 13791–13798 (1993); Bernardi, *J. Biol. Chem.*, 267, 8834–8839 (1992)), or a combination of PhAsO plus UDCA. When mitochondria were coincubated with 500 $\mu$M UDCA and 80 $\mu$M PhAsO, the MPT was reduced by approximately 50% compared to PhAsO alone p<0.001) (FIG. 8A). Moreover, DCA-induced mitochondrial swelling was inhibited by>45% with 5 $\mu$M cyclosporine A, a known inhibitor of the megapore channel. Finally, coincubation with both UDCA and cyclosporine did not produce an additive effect, suggesting that they inhibited MPT by similar mechanisms. Thus, the data indicate that both the induction of MPT by DCA and its inhibition by UDCA in isolated rat liver mitochondria are dose-dependent. Moreover, the ability of UDCA to act as a general inhibitor of the megapore form of MPT appears to be bile acid-specific and is not simply a property of its hydrophilicity.

UDCA Inhibits Disruption of $\Delta\Psi_m$ and ROS Production. FACscan analysis confirmed the existence of mitochondrial perturbation during treatment of isolated mitochondria with DCA. Significant changes were detected in both $\Delta\Psi_m$ and ROS production when isolated mitochondria were exposed to 100 $\mu$M DCA for 5 min in the presence or absence of 500 $\mu$M UDCA. As shown in FIG. 9A, the percentage of low $\Delta\Psi_m$ was increased after DCA treatment (16.0±1.8% vs. 13.1±2.4%). Incubation with UDCA alone produced no significant changes in $\Delta\Psi_m$ compared to controls. Moreover, UDCA protected against the DCA-induced increase in the percentage of low $\Delta\Psi_m$ (10.3±0.7%; p<0.05). Disruption of $\Delta\Psi_m$ with DCA was closely followed by an increased production of the ROS superoxide anion, as measured by dihydroethidium oxidation to ethidium (FIG. 9B). Superoxide anion production was significantly increased after DCA treatment (20.7±2.4% vs. 13.8±0.8%;p<0.01) and slightly decreased after UDCA incubation alone (11.8±2.8%). Furthermore, UDCA inhibited the production of superoxides induced by DCA (15.9±1.5%, p<0.05). Generation of other ROS, including hydrogen peroxide and hydroxyl radical measured using $H_2DCFDA$ was also substantially increased during DCA incubation compared to untreated mitochondria (FIG. 9C). Conversely, incubation with UDCA alone slightly decreased the percentage of other ROS. When the two bile acids were combined, UDCA completely prevented the changes associated with the hydrophobic bile acid (21.7±3.5% vs. 14.7±1.4%, p<0.05).

When mitochondria were coincubated with 500 $\mu$M UDCA, $\Delta\Psi_m$ disruption was reduced by approximately 65% when compared with 80 $\mu$M PhAsO alone (FIG. 10A). Similarly, ROS production of superoxide anions and peroxides were reduced 100 and 55%, respectively, (FIGS. 10B and 10C) when UDCA was coincubated with PhAsO p<0.05, or lower). In contrast, coincubation of isolated mitochondria with 500 $\mu$M HDCA did not prevent DCA-mediated changes in $\Delta\Psi_m$ (FIG. 11A) and ROS production (FIGS. 11B and 11C). Also, no changes were observed with HDCA alone.

Modulation of apoptosis-Related Protein Expression with Bile Acid Feeding. To examine the potential chronic effect of bile acids on apoptosis-associated gene expression, we determined liver cytoplasmic and mitochondrial steady-state protein levels for Bcl-2, Bcl-$X_L$, Bax, and Bad. Cytoplasmic levels of the pro-apoptotic protein Bax showed no significant change across all groups of animals regardless of whether bile acids were included in the diet (FIG. 12). In contrast, Bad expression was increased approximately 2-fold with DCA, Interestingly, although UDCA alone decreased Bad expression, the combination of DCA+UDCA increased protein abundance 5-fold (p<0.001). The steady-state levels of the anti-apoptotic protein Bcl-2 remained invariant in all animals, while the expression of its homolog Bcl-$X_L$ increased after the administration of UDCA alone (p<0.05) or when it was combined with DCA. In contrast to these results, DCA feeding was associated with a 4.5-fold increase in mitochondrial-associated Bax (D<0.001) (FIG. 13). Combination feeding with UDCA prevented this dramatic change even though UDCA feeding alone increased Bax expression slightly above baseline. The pro-apoptotic protein Bad was detected in very low levels in mitochondria in all the bile acid fed groups relative to control. In fact, mitochondrial abundance of this protein was decreased to<15% control values after bile acid feeding p<0.001). The administration of DCA significantly increased the abundance of Bcl-2 in mitochondria relative to controls p<0.05) and UDCA (D<0.01) fed animals. However, combination a feeding of both bile acids decreased Bcl-2 expression to near baseline values. Finally, no significant changes were observed across all groups in mitochondrial abundance of the anti-apoptotic protein Bcl-$X_L$.

We also determined liver cytoplasmic protein levels for c-Myc, p53, and retinoblastoma, since alterations in their expression levels have been associated with hepatocyte apoptosis. Interestingly, bile acid feeding did not induce significant changes in cytoplasmic levels of the tumor suppressor p53 (data not shown). Similarly, no significant changes in cytoplasmic c-Myc or retinoblastoma levels were detected in any of the groups relative to controls.

Example III

Ursodeoxycholic Acid Inhibits Bax Translocation to the Mitochondrial Membrane

A. Materials and Methods

Cell culture and preparation of rat primary hepatocytes. Rat primary hepatocytes were isolated from male Sprague-Dawley rats (200–250 g) by collagenase perfusion as described by Mariash, et al., *J. Biol. Chem.* 261, 9583–9586 (1986). Briefly, rats were anesthesized with phenobarbitol and the livers were perfused with 0.05% collagenase. Hepatocyte suspensions were obtained by passing digested livers through 0.125 mm gauze and washing cells in modified Eagle's medium (MEM) (Life Technologies, Inc., Grand Island, N.Y.). Cell viability was determined by trypan blue exclusion and was typically 85 to 90%. After isolation, hepatocytes were resuspended in William's E medium (Life Technologies, Inc.) supplemented with 26 mM sodium bicarbonate, 23 mM HEPES, 0.01 U/mL insulin, 2 mM L-glutamnine, 10 nM dexamethasone, 5.5 mM glucose, 100 U/ml penicillin and 100 U/ml streptomycin and then plated on 35×10 mm PRIMARIA tissue culture dishes (Becton Dickinson Labware, Lincoln Park, N.J.) at 1.0×10$^6$ cells/ml. The cells were maintained at 37° C. in a humidified atmosphere of 5% $CO_2$ for 3 h. Plates were then washed with medium to remove dead cells, and medium containing 10% heat-inactivated FBS (55° C. for 30 min) was added (Atlanta Biologicals, Inc., Norcross, Ga.).

Incubation of cells with inducers of apoptosis. Freshly isolated rat hepatocytes were cultured for 3 h as described above and then incubated with William's E medium supplemented with either 50 $\mu$M DCA for 4 h, I nM TGF-$\beta$1 for 24 h, or 25 nM okadaic acid for 16 h, in the presence or absence of 100 $\mu$M UDCA, or no addition (control). The medium was gently removed at the indicated time points and scored for nonviable cells by trypan blue dye exclusion. The attached cells were fixed for morphologic assessment of apoptotic changes.

Morphological evaluation of apoptosis. The medium was gently removed at the indicated time points to prevent detachment of cells. Cells were fixed with 4% formaldehyde in PBS, pH 7.4, for 10 min at room temperature, incubated with Hoechst dye 33258 (Sigma Chemical Co., St. Louis, Mo.) at 5 mg/mL in PBS for 5 min, washed with PBS and mounted with PBS:glycerol (3:1, v/v). Fluorescence was visualized with a Zeiss standard fluorescence microscope (Carl Zeiss, Inc., Thornwood, N.Y.). Photographs were taken with Kodak Ektar-1000 film (Eastman Kodak Co.). Stained nuclei were scored by blind analysis and categorized according to the condensation and staining characteristics of chromatin. Normal nuclei were identified as noncondensed chromatin dispersed over the entire nucleus. Apoptotic nuclei were identified by condensed chromatin, contiguous to the nuclear membrane, as well as nuclear fragmentation of condensed chromatin. Three fields per dish of approximately 500 nuclei were counted; mean values are expressed as the percent of apoptotic nuclei.

Isolation of cytosol and mitochondrial fractions and determination of cytochrome c and Bax content. Freshly isolated rat hepatocytes were cultured for 3 hours as described above and then incubated with William's medium supplemented with either 50 $\mu$M of DCA for 4 h, 1 nM TGF-$\beta$1 for 24 h and 25 mM okadaic acid for 16 h, in the presence or absence of 100 $\mu$M UDCA, or no addition (control). Time-course experiments were also performed. Cells (1.0×10$^7$/ml) were harvested by centrifugation at 600×g for 5 min at 4° C. The cell pellets were washed once in ice-cold PBS and resuspended with 3 volumes of isolation buffer containing 20 mM Hepes-KOH, pH 7.5, 10 mM KCl, 1.5 mM MgCl$_2$, 1 mM sodium EDTA, 1 mM sodium EGTA, 1 mM dithiothreitol (DTT), supplemented with the COMPLETE protease inhibitor cocktail (Boehringer Mannheim Biochemicals, Inc., Indianapolis, Ind.) in 250 mM sucrose. After chiling on ice for 15 min, the cells were disrupted by 40 stokes of a glass homogeneizer and the homogenates were centrifuged twice at 2,500×g for 10 min at 4° C. to remove unbroken cells and nuclei. The mitochondria were pelleted by centrifugation at 12,000×g for 30 min at 4° C., resuspended in isolation buffer containing 250 mM sucrose and frozen at −80° C. The supernatants of the 12,000×g spin were removed, filtered through 0.2 Am and then 0.1 $\mu$m Ultrafree MC filters (Millipore) to give cytosolic protein, an frozen at −80° C. Mitochondrial and cytosolic proteins were separated on a 15% SDS-polyacrylamide electrophoresis gel, transferred to nitrocellulose membranes, and incubated with 15% H$_2$O$_2$ for 15 min at room temperature. Blots were sequentially incubated with 5% milk blocking solution, primary monoclonal antibody to cytochrome c (Pharmigen, San Diego, Calif.) at a dilution of 1:5,000, overnight at 4° C., and finally with secondary goat anti-mouse IgG antibody conjugated with horseradish peroxidase (Bio-Rad Laboratories, Hercules, Calif.) for 2 h at room temperature. For the determination of Bax translocation from the cytosol to mitochondria, the blots were probed with primary polyclonocal antibody to Bax (Santa Cruz Biotechnology, Santa Cruz, Calif.), and then with secondary anti-rabbit antibody conjugated with horseradish peroxidase. The membranes were processed for cytochrome c and Bax detection using the system commercially available under the trade designation ECL, from Amersham Life Science, Inc. (Arlington Heights, Ill.).

Mitochondria isolation. Low calcium liver mitochondria were isolated from adult male 200–250 g Sprague-Dawley rats as previously described by Botla et al., *J. Pharmacol. Exp. Ther.*, 272, 930–938 (1995) and Watajtys et al., *J. Biol. Chem.*, 267, 370–379 (1992). In short, animals were sacrificed by exsanguination under ether anesthesia and the livers removed and rinsed in normal saline. Approximately 10 g of minced liver was homogenized at a speed of 800 rpm using 6 complete up and down strokes with a speed controlled mechanical skill drill and a teflon pestle (Tri-R Model K4 1, Tri-R Instruments, Rockville Center, N.Y.) in an ice-cold solution of 70 mM sucrose, 220 mM mannitol, 1 mM EGTA and 10 mM HEPES, pH 7.4 as a 10% (wt/vol) homogenate. The homogenate was centrifuged at 600×g for 10 min at 4° C. in an SS-34 rotor in a Sorvall RC5C centrifuge (Sorvall Instruments, Newtown, Conn.), and the postnuclear supernatant was centrifuged at 7,000×g for 10 min at 4° C. The crude mitochondrial pellet was further purified by sucrose-percoll gradient centrifugation as described by Sokol et al., *Gastroenterology*, 99, 1061–1071 (1990). The pellet was resuspended in 2 mL of homogenate buffer, and 1 mL of the resuspended pellet was carefully layered onto a 35-mL self-generating gradient containing 0.25 $\mu$M sucrose, 1 mM EGTA and percoll (Pharmacia Fine Chemicals, Piscataway, N.J.) (75:25, vol/vol). The mitochondria were purified by centrifugation at 43,000×g for 30 min at 4° C. using a Beckman Ti60 rotor and a Beckman ultracentrifuge model L8-55 (Beckman Instruments, Inc., Schaumburg, Ill.). The clear supernatant solution removed and the lower turbid layer was resuspended in 30 mL of wash buffer containing 0.1 $\mu$M KCl, 5 mM 3-(N-morpholino)-propane sulfonic acid (MOPS), and 1 mM EGTA, at pH 7.4 and centrifuged at 7,000×g for 10 min at 4° C. The resulting mitochondria pellet was washed in wash buffer two times. A final wash was carried out in chelex-100-treated buffer (Bio-Rad Laboratories, Richmond, Va.; 200–400 mesh, potassium form) without EGTA. The pellet was suspended in 4 mL of chelex-100-treated resuspension buffer containing 125 mM sucrose, 50 mM KCl, 5 mM HEPES, and 2 mM KH2PO4. The usual yield of mitochondria was approximately 25 mg of protein per gram of liver tissue. Mitochondria were used for experiments within 3 h of isolation. Aliquots were removed for examining the purity of the mitochondria preparation.

Marker enzymes and protein analysis. Mitochondria fractions were analyzed for mitochondrial malate dehydrogenase, lysosomal N-acetyl-B-glucosaminidase, and microsomal esterase enzymes. Protein concentrations were determined using the Bio-Rad protein assay (Bio-Rad Laboratories) as recommended by the manufacturer.

Measurement of MPT and determination of cytochrome c content in supernatants and mitochondrial pellets after MPT. The MPT was assessed using a spectrophotometric assay measuring high amplitude rapid changes in mitochondria volume. Mitochondria (1 mg protein) were incubated in 1 ml of chelex- 100-treated respiration buffer (0.1 $\mu$M NaCl, 10 mM MOPS, pH 7.4) for 10 min at 25° C. and swelling was monitored at 540 nm in a Beckman DU 64 spectrophotometer. Malate and glutamate (1 mM) were added to initiate respiration, and 3 min later rotenone (5 $\mu$M), an inhibitor of complex I of the respiratory chain, was also added to the supension. Basal values of mitochondria absorbance were measured for 5 min, and the optical density was monitored for an additional 5 min after addition 200 μM DCA or 80 μM phenylarsine oxide (PhAsO; Sigma Chemical Co.). For the coincubation studies, mitochondria were preincubated with 5 μM CyA, or 500 μM UDCA, hyodeoxycholic acid, tauroursodeoxycholic acid, glycocholic acid (Sigma Chemical Co.), or glycoursodeoxycholic acid (Steraloids) for 5 min at 25° C. prior to initiation of the assay. Following MPT assays, mitochondria were spun down at 12,000×g for 3 min at 4° C. Aliquots (20 μl) of the supernatant and pellet were subjected to SDS-polyacrylamide gel electrophoresis (15%) for detection of cytochrome c release as described above.

Electron microscopy. The mitochondrial pellet after the MPT assay was fixed overnight in 6% glutaraldehyde in cacodylate buffer, pH 7.2. The mitochondria were then rinsed with 0.1 μM PIPES buffer, followed by a 20 min postfix in cacodylated-buffered 2% $OsO_4$. Next, the mitochondria were dehydrated in progressive concentrations of ethanol followed by 100% propylene oxide, and embedded in Epon 812/Aralide resin. Sections (70–100 nm) were cut, placed on 200 nm copper grids and stained with lead citrate. The morphology of the isolated mitochondria after the MPT assays was studied by taking micrographs using a JEOL electron microscope at 80 Kv.

Detection of caspase 3 activity. The assay is based on the ability of the active enzyme to cleave the chromophore p-nitroanilide (pNA) from the enzyme substrate N-acetyl-Asp-Glu-Val-Asp-pNA (DEVD-pNA) (Sigma Chemical Co.). The proteolytic reaction was carried out in extraction buffer, containing 20 μg of cytosolic protein and 50 μM DEVD-pNA. The reaction mixtures were incubated at 37° C. for 1 h, and the formation of pNA was measured at 405 nm using a 96-well plate reader.

Measurement of mitochondrial membrane potential Mitochondrial energization was determined as the retention of the dye 3,3'-dihexyloxacarbocyanine (DiOC6(3); Molecular Probes Inc, Eugene, Oreg.). Primary rat hepatocytes were loaded with 100 nM DiOC6(3) during the last 30 min of treatment with TGF-β1, okadaic acid, or deoxycholic acid, in the presence or absence of UDCA. The supernatant was removed and the pellet washed twice in ice-cold-PBS. The pellet was the lysed by the addition of 600 μL of deionized water followed by homogeneization. The concentration of retained $DiOC_6(3)$ was read on a Perkin-Elmer LS-5 fluorescence spectrophotometer at 488 nm excitation and 500 nm emission.

Determination of PARP cleavage. For the determination of PARP cleavage, total protein were separated on a 8% SDS-polyacrylamide electrophoresis gel. Blots were probed with primary polyclonal antibody to PARP (Santa Cruz Biotechnology).

Densitometry. Video densitometry was accomplished using a Macintosh II (Apple Computer, Cupertino, Calif.) coupled to a Data Translation DT2255 video digitizer (Data Translation, Marlboro, Mass.) and a JVC GX-N8 video camera (JVC Corporation of America, Elmwood Park, N.J.). Quantitation of the autoradiograms used the NIH Image 1.4 densitometric analysis program.

Statistical analysis. Statistical analysis was performed using InStat version 2.1 for the ANOVA and Bonferroni's multiple comparison tests. Unless otherwise indicated, results are expressed as mean values i standard deviation (S.D.).

B. Results

Ursodeoxycholic acid (UDCA) plays a central role in modulating the apoptotic threshold in both hepatic and non-hepatic cells. The results indicated that the inhibition of mitochondrial membrane permeability transition (MPT) is one pathway by which UDCA protects against cell death. Mitochondrial cytochrome c translocates to the cytosol of cells undergoing apoptosis, where it participates in the activation of DEVD-specific caspases. The apoptotic protein Bax may produce cell death upon induction of MPT, which in turn causes release of cytochrome c from the mitochondria. Here, we demonstrated that the mitochondria depolarization induced by deoxycholic acid, TGF-β1 and okadaic acid was accompanied by the release of cytochrome c from the mitochondria, caspase-3 activation in the cytosol, and cleavage of the nuclear enzyme PARP, all of which were markedly inhibited by UDCA. Moreover, UDCA partially prevented the translocation of Bax from the cytosol to the mitochondria observed during apoptosis.

The percentage of apoptotic cells in isolated hat hepatocytes increased from 2% in the control to 7%, 30%, and 75% after incubation with 50 μM deoxycholic acid for 4 hours, 1 nM TGF-β1 for 24 hours, and 25 nM okadaic acid for 16 hours, respectively ($P<0.001$). Coincubation of 100 μM UDCA with each of the apoptosis-inducing agents was associated with a>80% inhibition of apoptosis ($P<0.001$). The loss of mitochondrial membrane potential in intact cells induced by deoxycholic acid, TGF-β1 and okadaic acid was accompanied by a progressive release of cytochrome c to the cytosol and a concomitant decrease in the content of cytochrome c in the mitochondria. Cytochrome c release to the cytosol and its depletion from the mitochondria were inhibited by 60% and 70% in the presence of UDCA, respectively ($P<0.001$). Furthermore, UDCA reduced the release of cytochrome c in isolated mitochondria associated with both deoxycholic acid and phenylarsine oxide by 70% and 65%, respectively ($P<0.001$), concomitant with its effect on reducing MPT. Inhibition of deoxycholic acid-induced MPT and cytochrome c release were also observed when taurine- and glycine-conjugated derivatives of UDCA were added to isolated mitochondria. Similarly, cyclosporine A, an inhibitor of the megapore channel, reduced deoxycholic acid-induced mitochondria swelling and cytochrome c release. TGF-P 1 and okadaic acid did not induce mitochondria swelling nor did they cause translocation of cytochrome c to the supernatants. Cleavage of the nuclear enzyme PARP by caspase-3 was also studied as another prominent indicator of apoptosis. Addition of deoxycholic acid, TGF- [] 1 and okadaic acid to isolated rat hepatocytes resulted in a progressive cleavage of PARP, while pretreatment with UDCA prevented this cleavage by 60% ($P<0.001$). Similarly, steady increases were observed in the caspase-3 activity of cytosolic extracts of primary hepatocytes treated with the inducers of apoptosis, an effect significantly prevented by UDCA ($P<0.001$).

We next questioned whether UDCA protective effects could be explained by its effect on preventing the redistribution of the proapoptotic molecule Bax from the cytosol to the mitochondria. Following induction of apoptosis, a 40%–70% decrease of cytosolic Bax was observed concomitant with a similar increase of mitochondrial Bax, while preincubation with UDCA prevented Bax translocation by 45% ($P<0.01$).

These data support a model in which mitochondrial membrane perturbation during apoptosis is modulated by UDCA. This hydrophilic bile acid prevents the translocation of Bax from the cytosol to the mitochondria thereby inhibiting other manifestations of apoptosis, such as release of cytochrome c, caspase activation with PARP cleavage, and nuclear fragmentation.

The complete disclosure of all patents, patent documents, and publications cited herein are incorporated by reference.

The foregoing detailed description and examples have been given for clarity of understanding only. No unnecessary limitations are. to be understood therefrom. The invention is not limited to the exact details shown and described, for variations obvious to one skilled in the art will be included within the invention defined by the claims.

What is claimed is:

1. A method for limiting apoptosis of a mammalian cell population, the method comprising contacting the cell population with an effective amount of an apoptotic limiting compound selected from the group of ursodeoxycholic acid, a salt thereof, an analog thereof, and a combination thereof, wherein the apoptosis is induced by a nonmembrane damaging agent.

2. The method of claim 1 wherein the nonmembrane damaging agent is selected from the group of TGF-β1, anti-Fas antibody, and okadaic acid.

3. The method of claim 1 wherein the cell population comprises hepatocytes.

4. The method of claim 1 wherein the cell population comprises astrocytes.

5. The method of claim 1 wherein the contacting step occurs in vitro.

6. The method of claim 1 wherein the contacting step occurs in vivo.

7. The method of claim 1 wherein the cell population is a human cell population.

8. The method of claim 1 wherein the step of contacting comprises administering to a patient an effective amount of an apoptotic limiting compound selected from the group of ursodeoxycholic acid, a salt thereof, an analog thereof, and a combination thereof.

9. The method of claim 8 wherein the apoptotic limiting compound is administered in combination with a pharmaceutically acceptable carrier.

10. The method of claim 9 wherein the step of administering comprises administering parenterally.

11. The method of claim 9 wherein the step of administering comprises administering orally.

12. A method for limiting apoptosis of a mammalian cell population, the method comprising contacting the cell population with an effective amount of an apoptotic limiting compound selected from the group of ursodeoxycholic acid, a salt thereof, an analog thereof, and a combination thereof, wherein the apoptosis is induced by ethanol.

13. A method for limiting apoptosis of a human cell population, the method comprising contacting the cell population with an effective amount of an apoptotic limiting compound selected from the group of hydrophilic bile acid, a salt thereof, an analog thereof, and a combination thereof, wherein the apoptosis is induced by a hydrophobic bile acid.

14. A method for limiting apoptosis of a mammalian cell population, the method comprising contacting the cell population with an effective amount of an apoptotic limiting compound selected from the group of hydrophilic bile acid, a salt thereof, an analog thereof, and a combination thereof, wherein the apoptosis is induced by TGF-β1, anti-Fas antibody, okadaic acid, or unconjugated bilirubin.

15. A method for inhibiting apoptosis associated with a nonliver disease in vivo, the method comprising administering ursodeoxycholic acid, a salt thereof, an analog thereof, or a combination thereof.

16. The method of claim 15 wherein the nonliver disease is an autoimmune disease, a cardiovascular disease, or a neurodegenerative disease.

17. A method of reducing expression of c-myc in a cell, the method comprising contacting the cell with an effective amount of ursodeoxycholic acid, a salt thereof, an analog thereof, or a combination thereof.

18. A method of increasing levels of Bcl-$X_L$ in a cell, the method comprising contacting the cell with an effective amount of ursodeoxycholic acid, a salt thereof, an analog thereof, or a combination thereof.

19. A method of inhibiting Bax translocation from the cytoplasm of a cell to a mitochondrial membrane, the method comprising contacting the cell with an effective amount of ursodeoxycholic acid, a salt thereof, an analog thereof, or a combination thereof.

20. A method for limiting apoptosis of a mammalian cell population, the method comprising contacting the cell population with an effective amount of an apoptotic limiting compound selected from the group of ursodeoxycholic acid, a salt thereof, an analog thereof, and a combination thereof, wherein the apoptosis is induced by a membrane damaging agent selected from the group consisting of unconjugated bilirubin, conjugated bilirubin, and a combination thereof.

21. The method of claim 20 wherein the cell population comprises hepatocytes.

22. The method of claim 20 wherein the cell population comprises astrocytes.

23. The method of claim 20 wherein the contacting step occurs in vitro.

24. The method of claim 20 wherein the contacting step occurs in vivo.

25. The method of claim 20 wherein the cell population is a human cell population.

26. The method of claim 20 wherein the step of contacting comprises administering to a patient an effective amount of an apoptotic limiting compound selected from the group of ursodeoxycholic acid, a salt thereof, an analog thereof, and a combination thereof.

27. The method of claim 26 wherein the apoptotic limiting compound is administered in combination with a pharmaceutically acceptable carrier.

28. The method of claim 27 wherein the step of administering comprises administering parenterally.

29. The method of claim 27 wherein the step of administering comprises administering orally.

* * * * *

UNITED STATES PATENT AND TRADEMARK OFFICE
CERTIFICATE OF CORRECTION

PATENT NO. : 6,544,972 B1
DATED : April 8, 2003
INVENTOR(S) : Steer et al.

It is certified that error appears in the above-identified patent and that said Letters Patent is hereby corrected as shown below:

Title page,
Item [56], References Cited, OTHER PUBLICATIONS,
"Rodrigues et al.," reference, insert before "Nov. 7-11," -- Abstract and Slides, Meeting, Am. Assn. for the Study of Liver Diseases, --; "Setchell et al.," reference, delete "*Gasroenterology*" and insert -- *Gastroenterology* --; and "Silva et al.," reference, delete "Asrocytes" and insert -- Astrocytes --

Column 1,
Line 44, delete "et al."

Column 2,
Line 1, delete "Bcl-1-2" and insert -- Bcl-2 --
Line 15, delete "et al."

Figure 1E:
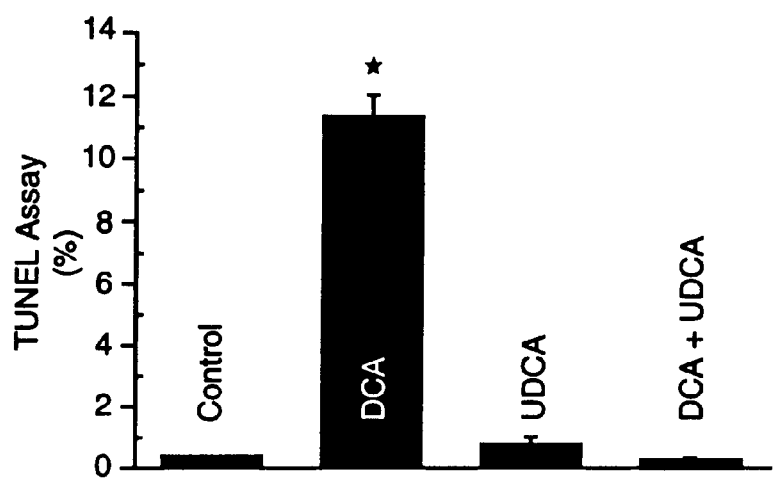
FIG. 1. Apoptosis in liver of rats fed bile acids. Animals were maintained for 10 days on standard rat chow supplemented with 0.4% of either DCA, UDCA, a combination of the two bile acids (DCA+UDCA), or no additional bile acid (control). On day 10, the livers were removed, rinsed in normal saline, flash-frozen in liquid nitrogen, and stored at −70° C. Liver tissue cryosections were prepared and then fixed and assayed for digoxigenin-labeled genomic DNA.

Column 3,
Line 55, delete "FIG.1" and insert -- Figures 1a-1e --
Line 63, delete "(FIG. 1A)"
Line 64, delete "(a)" and insert -- (Figure 1a) --
Line 64, delete "(b)" and insert -- (Figure 1b) --
Line 64, delete "(c)" and insert -- (Figure 2c) --
Line 65, delete "(d). (FIG.1B)" and insert -- (Figure 1d) --
Line 65, after "hepatocytes" insert -- (Figure 1e) --

Figure 5C:
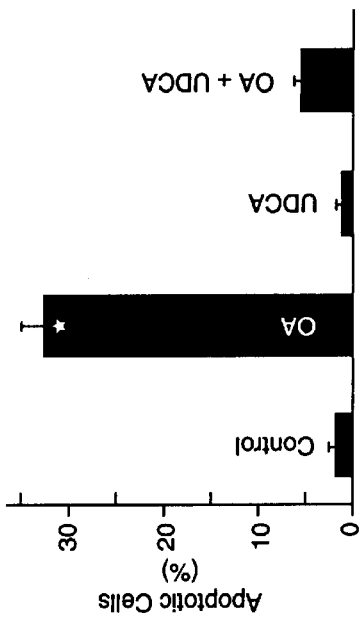
Figure 5D:
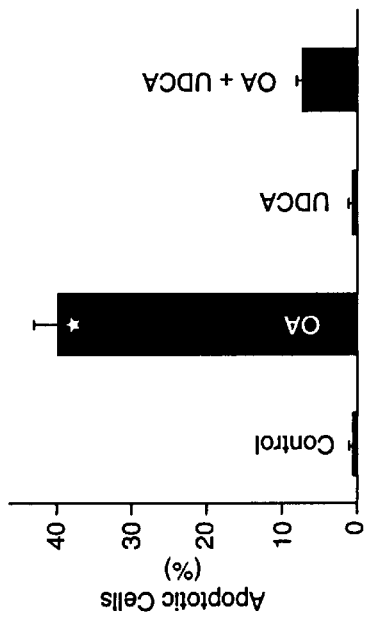
Figure 4C:
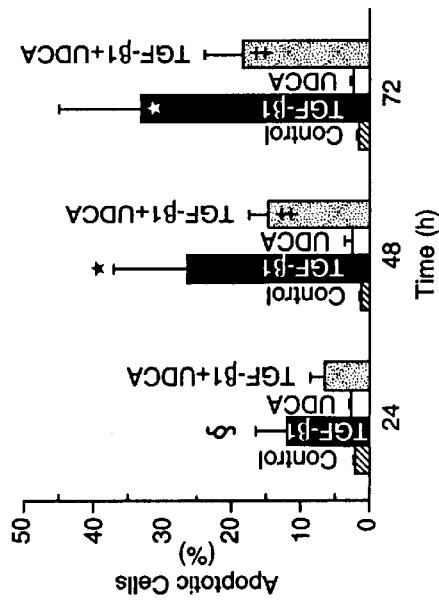
FIG. 4. UDCA inhibits apoptosis in HuH-7 cells incubated with TGF-β1 and in HepG2 cells treated with anti-Fas antibody. HuH-7 cells were grown with either 1 nM TGF-β1, 100 μM UDCA, a combination of the two, or no addition (control) in Dulbecco's MEM medium supplemented with 10% FBS.
Figure 4D:
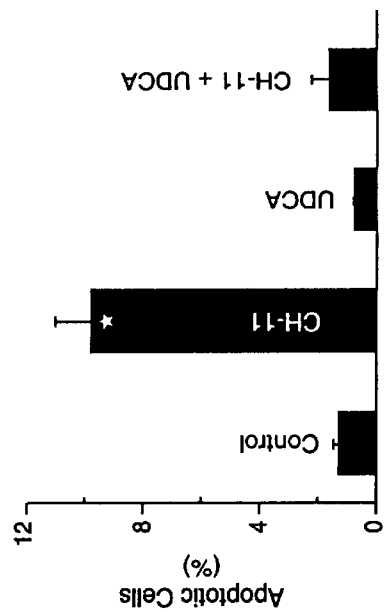

Column 4,
Line 3, delete "FIG. 2" and insert -- Figures 2a-2b --
Line 4, delete "(FIG. 1A)" and insert -- (Figure 2a) --
Line 13, delete "FBS ." and insert -- FBS. --
Line 28, delete "FIG. 4" and insert -- Figures 4a-4d --
Line 33, delete "(FIG. 4A)"
Line 34, delete "(a)" and insert -- (Figure 4a) --
Line 35, delete "(b)" and insert -- (Figure 4b) --
Line 35, delete "(lower panel)" and insert -- (Figure 4c) --
Line 36, delete "TGF-$\beta$ ," and insert -- TGF-$\beta$, --
Line 40, delete "(FIG. 4B)" and insert -- (Figure 4d) --
Line 50, delete "signifigant" and insert -- significant --
Line 52, delete "FIG. 5" and insert -- Figures 5a-5d --
Line 57, delete "(FIG."
Line 58, delete "5A, top)"
Line 58, delete "(a)" and insert -- (Figure 5a) --
Line 59, delete "(b)" and insert -- (Figure 5b) --
Line 61, delete "(FIGS. 5A and 5B, lower panel, $P<0.001$)" and insert -- (Figures 5c and 5d; $P<0.001$) --

UNITED STATES PATENT AND TRADEMARK OFFICE
CERTIFICATE OF CORRECTION

PATENT NO. : 6,544,972 B1
DATED : April 8, 2003
INVENTOR(S) : Steer et al.

It is certified that error appears in the above-identified patent and that said Letters Patent is hereby corrected as shown below:

Column 5,
Line 1, delete "FIG. 6" and insert -- Figures 6a-6b --
Line 8, delete "antiboby" and insert -- antibody --
Line 22, delete "(FIG. 7" and insert -- Figures 7a-7b --
Line 41, delete "$^{§}$p<5p<0.001" and insert -- $^{§}$p<0.001 --
Line 42, delete "FIG. 8" and insert -- Figures 8a-8b --
Line 60, delete "FIG. 9" and insert -- Figures 9a-9c --

Column 6,
Line 12, delete "p<0.05," and insert -- (p<0.05, --
Line 14, delete "FIG. 10" and insert -- Figures 10a-10c --
Line 33, delete "FIG. 11" and insert -- Figures 11a-11c --
Line 50, delete "FIG. 12" and insert -- Figures 12a-12d --
Line 56, before "and" insert -- (Figures 12a-12d) --
Line 57, delete "Representative" and insert -- For each of Figures 12a, 12b, 12c, and 12d, representative --
Line 62, delete "$^{517}$p<0.001" and insert -- $^{§}p$<0.001 --
Line 64, delete "FIG. 13" and insert -- Figures 13a-13d --

Column 7,
Line 3, before "and" insert -- (Figures 13a-13d) --
Line 4, delete "Representative" and insert -- For each of Figures 13a, 13b, 13c, and 13d, representative --
Line 10, insert space before "from"
Line 24, delete "effect" and insert -- affect --

Column 8,
Line 38, delete "parental" and insert -- parenteral --

Column 10,
Line 23, delete "animals" and insert -- animal --
Line 48, delete "BC1-$X_L$" and insert -- Bcl-$X_L$ --

Column 11,
Line 63, delete "aneshtesized" and insert -- anesthetized --

Column 12,
Line 17, delete "aintained" and insert -- maintained --
Line 64, delete "50 KM" and insert -- 50 $\mu$M --
Line 67, delete "FM" and insert -- $\mu$M --

Column 13,
Line 64, delete "Gastroenterolozy" and insert -- Gastroenterology --

UNITED STATES PATENT AND TRADEMARK OFFICE
CERTIFICATE OF CORRECTION

PATENT NO. : 6,544,972 B1
DATED : April 8, 2003
INVENTOR(S) : Steer et al.

It is certified that error appears in the above-identified patent and that said Letters Patent is hereby corrected as shown below:

Column 14,
Line 18, delete "$\mu$M" and insert -- M --

Column 15,
Line 3, delete "(FIG. 1A)" and insert -- (Figures 1a-1d) --
Line 11, delete "(FIG.1B)" and insert -- (Figure 1e) --

Column 16,
Line 62, delete "(FIG. 4A,a)" and insert -- (Figure 4a) --
Line 65, delete "(FIG. 4A lower panel)" and insert -- (Figure 4c) --

Column 17,
Line 12, delete "FIG. 4B" and insert -- Figure 4d --
Line 25, delete "Figs. 5A and 5B" and insert -- Figures 5a-5d --

Column 18,
Line 57, delete "CHR-11" and insert -- CH-11 --
Line 66, delete "\p<0.01" and insert -- †P<0.01 --

Column 19,
Line 25, delete "2-6" and insert -- 2a-6b --
Line 64, delete "$\mu$M" and insert -- M --

Column 20,
Line 4, delete "$\mu$M" and insert -- M --
Line 5, delete "mM$^3$" and insert -- mM 3 --
Line 17, delete "βB" and insert -- β --
Line 31, after "Pastorino" insert -- et al. --
Line 34, delete "$\mu$M" and insert -- M --
Line 57, delete "$\mu$UDCA" and insert -- $\mu$M UDCA --

Column 21,
Line 10, delete "500 M" and insert -- 500 $\mu$M --

Column 23,
Line 17, delete "p<0.001)" and insert -- (p<0.001) --

Column 24,
Line 1, delete "apoptosis" and insert -- Apoptosis --
Line 8, delete "(FIG. 12)" and insert -- (Figures 12a-12d) --
Lines 18 and 28, delete "(D<0.001)" and insert -- (*p*<0.001) --
Lines 18 and 19, delete "(FIG. 13)" and insert -- (Figures 13a-13d) --
Line 28, delete "a"

UNITED STATES PATENT AND TRADEMARK OFFICE
CERTIFICATE OF CORRECTION

PATENT NO. : 6,544,972 B1
DATED : April 8, 2003
INVENTOR(S) : Steer et al.

It is certified that error appears in the above-identified patent and that said Letters Patent is hereby corrected as shown below:

Column 25,
Line 4, delete "I nM" and insert -- 1 nM --
Line 53, delete "Am" and insert -- $\mu$M --

Column 26,
Line 9, after "Watajtys" insert -- -Rhode --
Line 15, delete "K4 1" and insert -- K41 --
Lines 28, 36 and 61, delete "$\mu$M" and insert -- M --
Line 44, delete "KH2PO4" and insert -- $KH_2PO_4$ --
Line 61, delete "chelex- 100-treated" and insert -- chelex-100-treated --

Column 27,
Line 16, delete "$\mu$M" and insert -- M --
Lines 36 and 38, delete "DiOC6(3)" and insert -- $DiOC_6(3)$ --
Line 43, delete "homgeneization" and insert -- homogenization --
Line 62, delete "i" and insert -- ± --

Column 28,
Line 16, delete "hat" and insert -- rat --
Line 39, delete "TGF-P 1" and insert -- TGF-β1 --
Line 43, delete "TGF-[]1" and insert -- TGF-β1 --

Column 29,
Line 3, after "are" delete "."

Signed and Sealed this

Third Day of February, 2004

JON W. DUDAS
*Acting Director of the United States Patent and Trademark Office*